US 8,907,782 B2

(12) United States Patent
Baker et al.

(10) Patent No.: US 8,907,782 B2
(45) Date of Patent: Dec. 9, 2014

(54) MEDICAL DEVICES WITH PROXIMITY DETECTION

(75) Inventors: Steven D. Baker, Beaverton, OR (US); Braxton L. Lathrop, Lake Oswego, OR (US); Soundharya Nagasubramanian, Portland, OR (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 137 days.

(21) Appl. No.: 13/225,989

(22) Filed: Sep. 6, 2011

(65) Prior Publication Data
US 2012/0003933 A1    Jan. 5, 2012

Related U.S. Application Data

(63) Continuation-in-part of application No. 12/827,817, filed on Jun. 30, 2010.

(51) Int. Cl.
| | |
|---|---|
| *H04W 76/06* | (2009.01) |
| *H04W 76/02* | (2009.01) |
| *H04W 74/02* | (2009.01) |
| *G06F 19/00* | (2011.01) |
| *H04W 4/02* | (2009.01) |
| *H04L 29/08* | (2006.01) |
| *A61B 5/00* | (2006.01) |
| *H04W 74/06* | (2009.01) |

(52) U.S. Cl.
CPC .......... *H04W 76/023* (2013.01); *H04W 76/068* (2013.01); *H04W 74/02* (2013.01); *G06F 19/322* (2013.01); *H04L 67/14* (2013.01); *A61B 5/002* (2013.01); *H04W 74/06* (2013.01); *A61B 5/0002* (2013.01); *G06F 19/3418* (2013.01); *H04W 76/02* (2013.01); *G06F 19/34* (2013.01); *G06F 19/3412* (2013.01); *H04W 76/06* (2013.01); *H04W 4/02* (2013.01); *H04W 76/027* (2013.01)
USPC ...... 340/539.12; 342/450; 342/458; 455/41.3

(58) Field of Classification Search
CPC ... H04W 4/008; H04W 76/02; H04W 76/027; H04W 76/06; H04W 76/068; H04L 67/14
USPC .............. 340/539.12; 342/450, 458; 455/41.3
See application file for complete search history.

(56) References Cited

U.S. PATENT DOCUMENTS

| 4,893,073 A | 1/1990 | McDonald |
|---|---|---|
| 5,559,433 A | 9/1996 | Onizuka |

(Continued)

FOREIGN PATENT DOCUMENTS

| KR | 10-2009-0011863 | 2/2009 |
|---|---|---|
| KR | 10-2009-0059324 | 6/2009 |

(Continued)

OTHER PUBLICATIONS

Application filed in U.S. Appl. No. 12/827,817 on Jun. 30, 2010.

(Continued)

*Primary Examiner* — Daniel Wu
*Assistant Examiner* — Benyam Haile
(74) *Attorney, Agent, or Firm* — Merchant & Gould P.C.

(57) ABSTRACT

A wireless medical device is disclosed. The wireless medical device comprises a processor, a memory, a sensor for detecting a physiological signal, a radio and a proximity detector to measure a distance of the wireless medical device relative to a second wireless medical device. The proximity detector includes a ranging functionality. A wireless communication channel is created when a distance between the wireless medical device and the second wireless medical device is within a first predetermined threshold. The distance is greater than zero.

14 Claims, 9 Drawing Sheets

(56) References Cited

U.S. PATENT DOCUMENTS

| | | | |
|---|---|---|---|
| 5,928,227 A | 7/1999 | Howard et al. | |
| 6,356,584 B1 | 3/2002 | Cuylen | |
| 6,934,874 B2 | 8/2005 | Retter et al. | |
| 6,985,773 B2 | 1/2006 | Von Arx et al. | |
| 7,042,364 B2 | 5/2006 | Capobianco | |
| 7,099,283 B2 | 8/2006 | Matta et al. | |
| 7,197,357 B2 | 3/2007 | Istvan et al. | |
| 7,424,288 B2 | 9/2008 | Jung et al. | |
| 7,689,169 B2 | 3/2010 | Lee et al. | |
| 7,860,456 B2 | 12/2010 | Kim | |
| 7,973,657 B2 | 7/2011 | Ayed | |
| 7,978,062 B2 | 7/2011 | LaLonde et al. | |
| 8,179,124 B2 | 5/2012 | De Huu | |
| 2002/0008625 A1 | 1/2002 | Adams et al. | |
| 2002/0082480 A1 | 6/2002 | Riff et al. | |
| 2003/0033032 A1 | 2/2003 | Lind et al. | |
| 2003/0105499 A1 | 6/2003 | Hartley et al. | |
| 2003/0142651 A1 | 7/2003 | Matta et al. | |
| 2003/0149459 A1 | 8/2003 | Von Arx et al. | |
| 2003/0206116 A1 | 11/2003 | Weiner et al. | |
| 2004/0015058 A1 | 1/2004 | Besson et al. | |
| 2004/0073127 A1 | 4/2004 | Istvan et al. | |
| 2004/0102683 A1 | 5/2004 | Khanuja et al. | |
| 2004/0202339 A1 | 10/2004 | O'Brien, Jr. et al. | |
| 2004/0225199 A1 | 11/2004 | Evanyk et al. | |
| 2004/0249257 A1 | 12/2004 | Tupin, Jr. et al. | |
| 2004/0249258 A1 | 12/2004 | Tupin, Jr. et al. | |
| 2005/0068173 A1 | 3/2005 | Capobianco | |
| 2005/0097191 A1 | 5/2005 | Yamaki et al. | |
| 2005/0261556 A1 | 11/2005 | Such et al. | |
| 2006/0025834 A1 | 2/2006 | Von Arx et al. | |
| 2006/0115066 A1 | 6/2006 | Levien et al. | |
| 2006/0135065 A1 | 6/2006 | Lee et al. | |
| 2006/0179079 A1 | 8/2006 | Kolehmainen | |
| 2006/0212085 A1 | 9/2006 | Fischell et al. | |
| 2006/0219776 A1 | 10/2006 | Finn | |
| 2007/0003061 A1 | 1/2007 | Jung et al. | |
| 2007/0010748 A1 | 1/2007 | Rauch et al. | |
| 2007/0032832 A1 | 2/2007 | Feher | |
| 2007/0070035 A1* | 3/2007 | Asbury et al. | 345/156 |
| 2007/0135866 A1 | 6/2007 | Baker et al. | |
| 2007/0162089 A1 | 7/2007 | Mosesov | |
| 2007/0264988 A1 | 11/2007 | Wilson et al. | |
| 2008/0005288 A1 | 1/2008 | Kodama et al. | |
| 2008/0013601 A1 | 1/2008 | Lind et al. | |
| 2008/0046039 A1 | 2/2008 | Corndorf | |
| 2008/0140160 A1 | 6/2008 | Goetz et al. | |
| 2008/0151695 A1 | 6/2008 | Kimmel et al. | |
| 2008/0177150 A1 | 7/2008 | Ii et al. | |
| 2008/0183245 A1 | 7/2008 | Van Oort et al. | |
| 2008/0183910 A1 | 7/2008 | Natoli et al. | |
| 2008/0191866 A1 | 8/2008 | Falck | |
| 2008/0227393 A1* | 9/2008 | Tang et al. | 455/41.3 |
| 2008/0228045 A1 | 9/2008 | Gao et al. | |
| 2008/0234557 A1 | 9/2008 | Demharter | |
| 2008/0281169 A1 | 11/2008 | Akkermans et al. | |
| 2008/0281170 A1 | 11/2008 | Eshelman et al. | |
| 2008/0287748 A1 | 11/2008 | Sapounas et al. | |
| 2009/0018453 A1 | 1/2009 | Banet et al. | |
| 2009/0023391 A1 | 1/2009 | Falck | |
| 2009/0030285 A1* | 1/2009 | Andersen | 600/300 |
| 2009/0069642 A1 | 3/2009 | Gao et al. | |
| 2009/0076343 A1 | 3/2009 | James et al. | |
| 2009/0076348 A1 | 3/2009 | Manicka et al. | |
| 2009/0076350 A1 | 3/2009 | Bly et al. | |
| 2009/0088605 A1 | 4/2009 | Ross et al. | |
| 2009/0096573 A1 | 4/2009 | Graessley | |
| 2009/0112630 A1 | 4/2009 | Collins, Jr. et al. | |
| 2009/0118595 A1 | 5/2009 | Greiner et al. | |
| 2009/0140923 A1* | 6/2009 | Graves et al. | 342/450 |
| 2009/0215398 A1 | 8/2009 | Adler et al. | |
| 2009/0227282 A1 | 9/2009 | Miyabayashi et al. | |
| 2009/0231125 A1 | 9/2009 | Baldus et al. | |
| 2009/0239587 A1 | 9/2009 | Negron et al. | |
| 2009/0275296 A1 | 11/2009 | Huang et al. | |
| 2009/0305212 A1 | 12/2009 | McKenzie et al. | |
| 2010/0010338 A1 | 1/2010 | van Dam et al. | |
| 2010/0029205 A1 | 2/2010 | Lu et al. | |
| 2010/0045425 A1 | 2/2010 | Chivallier | |
| 2010/0082983 A1 | 4/2010 | Shah et al. | |
| 2010/0082990 A1 | 4/2010 | Grigorovitch | |
| 2010/0125188 A1 | 5/2010 | Schilling et al. | |
| 2010/0145165 A1 | 6/2010 | Merry | |
| 2010/0234720 A1 | 9/2010 | Tupin, Jr. et al. | |
| 2010/0297946 A1 | 11/2010 | Alameh et al. | |
| 2011/0018854 A1 | 1/2011 | Barclay et al. | |
| 2011/0105861 A1 | 5/2011 | Derchak et al. | |
| 2011/0152632 A1 | 6/2011 | Le Neel et al. | |
| 2011/0160786 A1 | 6/2011 | Stubbs et al. | |
| 2011/0183698 A1 | 7/2011 | Hoctor et al. | |
| 2011/0202371 A1* | 8/2011 | Darguesse et al. | 705/3 |
| 2011/0210820 A1 | 9/2011 | Talty et al. | |
| 2011/0213216 A1 | 9/2011 | McKenna et al. | |
| 2011/0288379 A1 | 11/2011 | Wu | |
| 2014/0128674 A1 | 5/2014 | Wieters | |

FOREIGN PATENT DOCUMENTS

| | | |
|---|---|---|
| KR | 10-2009-0059324 A | 6/2009 |
| WO | WO 2006/047400 | 5/2006 |
| WO | 2011115717 A1 | 9/2011 |

OTHER PUBLICATIONS

International Search Report & Written Opinion in PCT/US2012/051830 mailed Feb. 1, 2013, 10 pages.

Agrafioti et al.: On Supporting Anonymity in a Ban Biometric Framework; Digital Signal Processing, Aug. 18, 2009; © 2009 IEEE; 6 pgs.

Antoniou et al.; "iTouch: RFID Middleware for Boosting Connectivity & Intuitive User Interaction in Smart Spaces", May 9, 2006, 34 pages.

U.S. Appl. No. 12/723,726, filed Mar. 15, 2010.

Cho et al.; Opportunistic Medical Monitoring Using Bluetooth P2P Networks, Jun. 2008, 6 pages.

Chowdhury et al.: Context-aware Data Association and Authenticity in Pervasive Healthcare; Dec. 1, 2009; © 2009 IEEE Computer Society; pp. 227-230.

Falck et al.: Plug 'n Play Simplicity for Wireless Medical Body Sensors; Mobile Netw Appl, vol. 12 Issue 2-3, Jul. 25, 2007; © Springer Science + Business Media, LLC; pp. 143-153.

International Search Report and Written Opinion in PCT/US2011/024853, mailed Aug. 2, 2011, 10 pages.

Kostelnik et al.; BlueMedica—Wireless Medical Data Access Appliance, 2008, 7 pages.

OLLA: Mobile Health Technology of the Future: Creation of an M-Health Taxonomy Based on Proximity; Int. J. Healthcare Technology and Management, vol. 8, Nos. 3-4; © 2007 Inderscience Enterprises Ltd.; pp. 370-387.

* cited by examiner

MEDICAL DEVICES WITH PROXIMITY DETECTION

CROSS REFERENCE TO RELATED APPLICATION

This application is a continuation-in-part application of, and claims the priority and benefit to, U.S. patent application Ser. No. 12/827,817, entitled "Body Area Network Body Improvements for Clinical Workflows," filed Jun. 30, 2010, the entirety of which is hereby incorporated by reference.

BACKGROUND

Personal area networks in a medical setting permit sensor data from a patient to be efficiently transmitted to a display device. Many such networks use Bluetooth technology both in sensors attached to the patient and in the display device. Each Bluetooth sensor is typically paired to the display device to enable the transmission of sensor data to the display device.

In order for a Bluetooth sensor to be paired to a display device, power must be applied to both the Bluetooth sensor, including the sensor radio, and the display device including, the display device radio. Each radio must be in a connectable mode. Further, if the radios in the sensor and display device are not aware of each other, at least one radio must also be in a discoverable state. Typically, wireless sensors operate on battery power. It is desirable that a mechanism for applying power to a wireless sensor be easy to use, minimize drainage of the battery, connect to the desired display device and ensure that the patient be correctly identified.

In a medical setting, it is important that sensor devices are correctly identified to ensure that the sensor devices are placed on the correct patient. If the sensor devices are wired, the patient identification is usually not an issue, since the wire is run from the sensor directly to the monitoring device. However, wireless sensor devices typically do not provide any patient context, e.g., room number, patient ID, patient history, when attached to a patient, so identification of the correct wireless sensor devices with the correct monitoring devices can be an issue.

SUMMARY

Aspects of the disclosure are directed to a wireless medical device. The wireless medical device comprises a processor, a memory, a sensor for detecting a physiological signal, a radio and a proximity detector to measure a distance of the wireless medical device relative to a second wireless medical device. The proximity detector includes a ranging functionality. A wireless communication channel is created when a distance between the wireless medical device and the second wireless medical device is within a first predetermined threshold. The distance is greater than zero.

In another aspect, a method is disclosed for authenticating a connection between two wireless medical devices. A first wireless medical device is moved to the proximity of a second wireless medical device. A first proximity detector on the first wireless medical device is used to determine a distance between the first wireless medical device and the second wireless medical device. Authentication of a connection between the first wireless medical device and the second wireless medical device is allowed when a distance between the first wireless medical device and the second wireless medical device is within a first predetermined threshold. The distance is greater than zero.

In another aspect, a system is disclosed for transmitting physiological data from a first wireless medical device. The system comprises the first wireless medical device and a patient monitor device. The first wireless medical device comprises a first processor, a first memory that stores a patient context and a first radio. The patient context provides an identifier for the patient. The first radio comprises a first ultra-wideband (UWB) transceiver that determines a first distance between the first wireless medical device and the patient monitor device. The first radio uses the first distance as part of an authentication process. The patient monitor device comprises a second processor, a second memory that stores the patient context and a second radio. The second radio comprises a second UWB transceiver. The first wireless medical device joins a personal area network with the patient monitor device when the first distance between the first wireless medical device and the patient monitor device is within a first predetermined threshold. The first distance is greater than zero. The first wireless medical device obtains the patient context from the patient monitor device. The patient context is obtained from the patient monitor device when the first distance between the first wireless medical device and the patient monitor device is within the first predetermined threshold for at least a first predetermined interval of time. The first wireless medical device transfers physiological data to the patient monitor. The physiological data is transferred along with the patient context. The patient context is removed from the first wireless medical device when the first wireless medical device is part of a spot workflow and when a second distance between the first wireless medical device and the patient monitor device is greater than a second predetermined threshold for at least a second predetermined interval of time.

The details of one or more techniques are set forth in the accompanying drawings and the description below. Other features, objects, and advantages of these techniques will be apparent from the description, drawings, and claims.

DETAILED DESCRIPTION

Figure 1:
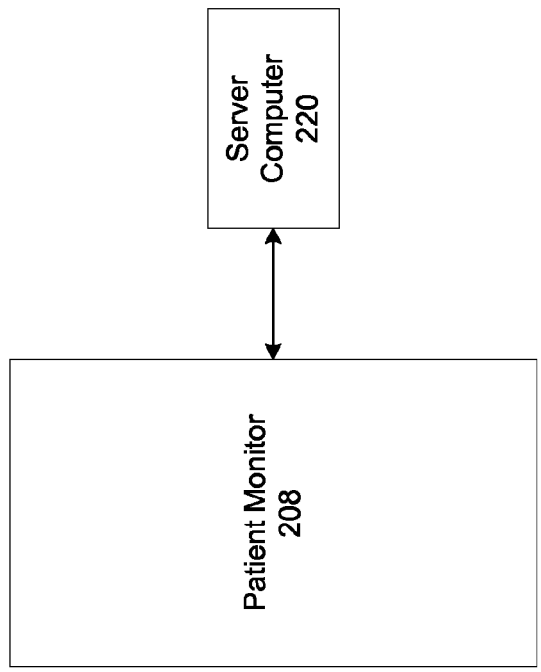
FIG. 1 shows an example personal area network for a medical application.
Figure 1:
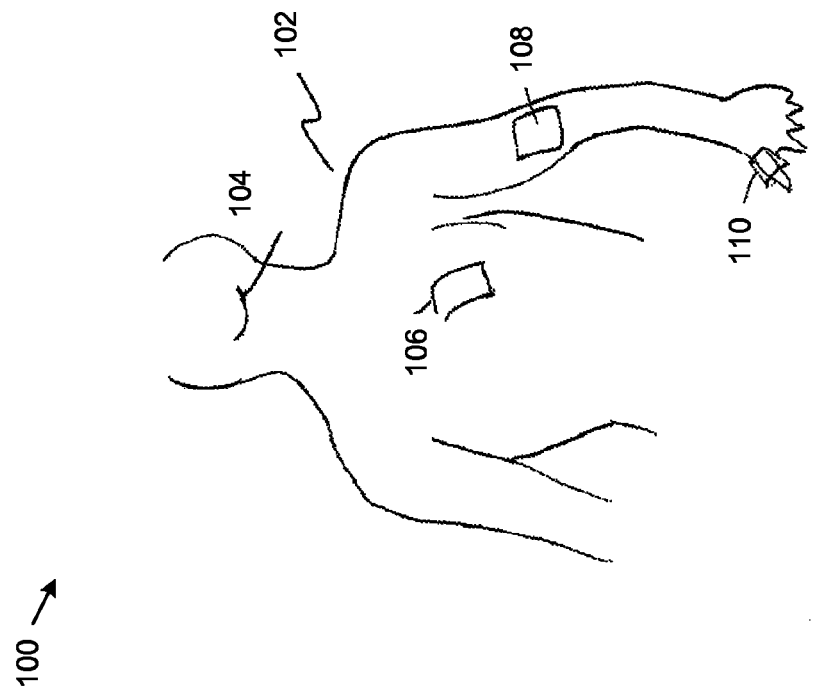

The present disclosure is directed to example systems and methods for pairing physiological sensor devices for a patient in a personal area network. Pairing is a term defined in the Bluetooth Specification and it is used analogously herein, applying the pairing concept to any radio. In the systems and methods, a proximity detector is used to enable devices to execute functions such as turning on power at a sensor device, turning on power to a radio in the sensor device, and enabling the radio device to making a radio connection between devices. Low-function proximity detectors may only detect proximity. Medium function proximity detectors may detect proximity and also transmit out-of-band data, and may be used for authentication. High function proximity detectors may also include ranging functions. The proximity detector turns the power on at the sensor device when the sensor device is in close proximity to a gateway device. The gateway device is typically a monitoring and display device that also provides access to a local or wide area network for transmitting sensor data to a server computer. The gateway device also includes a proximity detector. Typically, the gateway device includes a source of AC power so that the gateway device is generally powered on. However, in other examples, the gateway device may be battery operated and may not be powered on until the gateway device comes into proximity with a sensor device.

In example embodiments, the proximity detector on the sensor device provides a magnetic mechanism to activate power at the sensor device. Each proximity detector includes both a magnet and a magnetic detector. When the proximity detector on the sensor device is in close proximity with the proximity detector on the gateway device, the magnetic detector on the gateway device detects the magnet on the sensor device and the magnetic detector on the sensor device detects the magnet on the gateway device. Such a device has an advantage of very low power operation.

The detection of the magnet by the sensor device activates power on the sensor device and the detection of the magnet on the gateway device provides an indication to the gateway device that power is activated on the sensor device. In examples where the gateway device does not include AC power or in cases where the gateway device does include AC power but is powered off, the detection of the magnet on the gateway device activates power on the gateway device. Once power is activated on both the sensor device and the gateway device, a Bluetooth pairing sequence is initiated and the sensor device is paired to the gateway device.

If either the sensor device or the gateway device is already powered, then the proximity detection may power the radio, enable the radio and put the radio in a connectable state. If the radio in either the sensor device or the gateway device is already powered, then the proximity detection may put the radio in a connectable state.

Other proximity detectors may be used. If each device has a coil, magnetic coupling allows the coil in one device to detect if the coil in the other device has a current. One could pulse current in the first coil and detect the current pulse in the second coil. Detection of the current pulse in the coil of the first device by the coil of the second device would indicate proximity. A related solution with a magnet and a coil in the first device and a magnetic detector and a coil on the second device could have the second device detect proximity of the first device through actuation of the magnetic switch. The proximity detection causes the second device to enable its radio and also to pulse a current through its coil. This current pulse is detected in the first device, causing it to enable its radio. Alternately, placing a load on the receiving coil in the second device allows the transmitting coil to detect proximity of the receiving coil as reflected impedance of the receiving coil's load affects the current and voltage in the transmitting coil. Modulating the load modulates the current and voltage of the transmitting coil, allowing data to be transmitted from the second device to the first device. Proximity detection may be accomplished through time stamps of related signals, such as acceleration when two devices are tapped together. A time stamp on the signals can be used as a filter to ensure that the two devices were tapped at close to the same time. Alternately, a device may require a specific sequence such as three taps before enabling the radio. Optical signals (IR, UV, or Visible) from one device may be received by the second and these could be both detected by the second device and be reflected back to the first device. By encoding the optical signal, one may confidently assume the signal is authentic. A resistive detection could be used to detect if one device touches another as could one-wire serial where making electrical contact causes one device to transmit data to the other, where the data may include a Media Access Control (MAC) address and other out of band communication such as a link key or PIN. Capacitive touch switches may be placed on a printed circuit board or embedded in the plastic cases creating a hidden switch that is activated when a hand is brought nearby. Ultrasonic transceivers, Ultra-Wideband (UWB) and RFID may be used for both proximity detection and communication of out of band data. For example, UWB can be used to determine if the range between two radios is less than 25 cm and only then allow the radios to connect. By only allowing the connection between devices at close range, connections by devices external to the facility can be prevented.

The term "out-of-band" refers to communications which occur outside of a primary communication method or channel. In the UWB example, if authentication is a function of range and ranging is a secondary aspect of the UWB transceiver (the primary aspect being transmission of data), then the ranging used for authentication is an example of out-of-band communication. Using received signal strength to infer relative distances between devices would be considered an out-of-band communication of distance. Out-of-band may also refer to using a second channel supported by a transceiver. For example, standard data may be transmitted on a first channel and high priority data may be transmitted on a second channel. As a second example, data may be transmitted on a first channel and descriptors such as patient ID or annotations for the data may be transmitted on a second channel. As a third example, BlueTooth might use 802.11 for authentication, there, 802.11 is the out-of-band communication channel. The term "authentication" refers to a process by which a first device is able to confirm the identity of a second device and/or to confirm that the second device should be trusted. Authentication may be unidirectional or bidirectional.

The systems and methods of the present disclosure may also use contextual data to determine when to change the radio state to connectable or connectable and discoverable. For example, a sensor may assume that it is in range of a gateway whenever the sensor is powered, whenever a new measurement is requested or when other contextual events occur and automatically put its radio in a discoverable and connectable state. Other contextual events include one or more of: losing connection to a previous gateway, detecting a new gateway, detecting a decrease in received power from the current gateway, detecting an increase in received power from a new gateway, detecting a change in range to a gateway, and receiving new patient information. Specific contextual events to be considered depend on the clinical workflow, as discussed later herein.

A personal area network is a computer network used for communication between computer devices close to an individual person. A personal area network may also be referred to as a body area network when the personal area network is a collection of physiological sensors and monitors. In this disclosure, pairing refers to Bluetooth pairing and also to equivalent transmission of credentials and information, such as an address, required to establish a radio connection. These credentials may include authentication credentials, such as public keys and nonces that may be used to authenticate devices for secure, authenticated data transfer.

In a medical setting, a personal area network may include physiological sensor devices attached to a patient that are used to monitor health parameters of the patient. Some examples of physiological sensor devices used in a medical setting are blood pressure monitoring devices, thermometers, ECG sensors, EEG sensors, cardiac output sensors, $ETCO_2$ sensors, oxygen saturation sensors ($SPO_2$), glucometers, weight scales, and blood pressure sensors. Other types of sensor devices can be used. The sensor devices typically transmit sensor data over a network to a patient monitoring device, such as a wall-mounted display unit or a central station, such as the ACUITY® Central Monitoring System from Welch Allyn, Inc. of Skaneateles Falls, N.Y. A personal area network may also include a smart phone such as an iPhone manufactured by Apple Computer, Inc. of Cuppertino, Calif. or a Personal Digital Assistant (PDA), perhaps used by a clinician to interact with the patients' personal area networks such as the Clinician Notifier product from Welch Allyn, Inc. of Skaneateles Falls, N.Y. The PDA could join a patient network either using a menu-based system as is common for Bluetooth connections today or it could have a proximity detector that causes the PDA to join the personal area network.

One type of radio device used in a wireless personal area network is a Bluetooth radio. Bluetooth is a wireless technology that can be used in personal area networks to transmit and receive data over short distances (generally less than 30 feet, although data can be transmitted up 100 meters depending on device class). Bluetooth uses a layered protocol architecture consisting of four core layers and associated protocols. The physical layer is the lowest layer in each Bluetooth device and is instantiated as a radio frequency ("RF") layer that includes a transceiver with transmit and receive capability. Bluetooth uses the microwave radio spectrum in the 2.402 GHz to 2.4835 GHz range.

Bluetooth devices are peer devices, each including a Bluetooth radio and the four core protocol layers. However, when two or more Bluetooth devices are connected in a personal area network, one device can become a master device and the remaining devices then become slave devices. A master Bluetooth device can communicate with up to seven slave devices. However, a slave can switch roles and become a master at any given time. A Bluetooth device may be a slave in one personal area network and a master in a second personal area network. Later version of the Bluetooth specification, such as Bluetooth LE, provide for a larger set of peer devices.

Because Bluetooth is a wireless technology, the integrity and privacy of the transmitted data are a concern. To improve the integrity and privacy of data transmission, Bluetooth permits two devices to be paired with each other where the devices transmit on an encrypted link so that they can securely communicate with each other. Once two devices are paired, they can connect and communicate with each other without additional user intervention. The pairing process is typically initiated the first time a device receives a connection request from a device to which it is not already paired. During the discovery process Bluetooth addresses of each device are shared and during the pairing process, a shared secret key, known as a link key, is generated by the two devices. This link key is used to generate an encryption key, which is used to encrypt data for the current session. If the link key is stored along with the Bluetooth address of the peer device, then the devices are bonded so that the pairing information can be used in the future, even if the device(s) has been power cycled or if the devices have been out of range of each other. If either device deletes the link key, pairing must occur again before communication can occur. At the start of each communication session, the link key is used in a process to cryptographically authenticate the identity of the device, and be sure that it is the same device with which it previously paired.

In a wireless personal area network, sensor data is transmitted using a wireless data exchange protocol, such as Bluetooth, to a central point, called a hub. Often, this central point has a connection to a larger network, such as an 802.3 or 802.11 LAN. In this disclosure, a hub with a connection to a different type of network is called a bridge or a gateway.

In a wireless personal area network for monitoring sensor data, each sensor device may be joined to the network. In Bluetooth, joining a network when none of the network information is known requires discovery to learn the Bluetooth address of the other device, connection to initiate communication, and pairing to generate a shared secret key for authentication and encryption. While this disclosure uses Bluetooth as an example personal area network, any network, including 802.15.4, Bluetooth LE, ZigBee, UWB, a low-power 802.11 network, Wi-Fi™ Direct, or a proprietary network could be used. Other physical media such as IR as disclosed in the IEEE 802.11-1999 standard and ultrasonic may be used in lieu of RF. Of these, some technologies allow for ranging and ranging allows proximity detection. These include at least UWB, IR, and Ultrasound.

A hub to which multiple sensors are paired that includes a display to show the physiological state of the patient is a patient monitoring device. This type of hub typically has a local area network uplink, making the patient monitoring device a bridge. Any RF enabled device with a processor and display, including a PDA, cellular phone, PC, or laptop can operate as a hub and also as a patient monitor. The appropriate pairing of a sensor device with a patient monitoring device ensures that the sensor data is properly transmitted to the correct monitoring device. This is particularly important in a medical setting that may include a plurality of patients, sensors, monitoring devices and personal area networks to ensure that a particular patient's physiological data is tagged with the correct patient identifier. The patient identifier may be encrypted independent of any encryption that occurs automatically on the communication link to further ensure protection of electronic personal health information.

The procedure for pairing a sensor device to a monitoring device typically requires a user to manually enter data to authenticate that the proper devices are connecting in order to complete the pairing. For example, using Bluetooth 2.0, the two devices that pair require that the same PIN is presented to both devices. For some limited functionality devices, such as headsets, the PIN for the headset may be hard coded into the headset and the user enters the PIN into the device to be paired, e.g., a cellular telephone. Since no data are transacted prior to PIN entry and the PIN is not transmitted, this process verifies that the user intends the two devices to establish a connection. This solution works reasonably well if the device is only to be paired once. The PIN solution also has security and usability issues, particularly as implemented. For example, the PIN for most headsets is an easy to remember number such as 0000 or 9999, so an intruder can guess the PIN and masquerade as the intended device. In addition, a brute force attack requires only 10,000 different sequences (Although Bluetooth 2.0 uses a 16-byte PIN, this is usually generated by augmenting a 4-digit PIN with part of the Bluetooth address of the device, which is known). If the use case requires pairings to be made, removed, and re-built as occurs in clinical applications, the time to enter the PIN and navigate menus may be cumbersome. The systems and methods described in the present disclosure permit sensor devices to be attached to a patient and paired to a monitoring device in an efficient and automated manner, thereby minimizing the need for a user to manually enter information.

An improved pairing mechanism introduced in Bluetooth Version 2.1+EDR is Secure Simple Pairing (SSP). SSP has four modes of operation: Numeric Comparison, Passkey Entry, Out-Of-Band (00B), and Just Works. With the first two modes, some degree of user intervention is required to either enter or compare numeric values that are computed as a function of the link key. In the third mode, an auxiliary set of transceivers must exist to transmit the Bluetooth pairing information. In the fourth mode, the devices assume that a user authentication step occurred and opens the device to a security risk, such as a man-in-the-middle (MITM) attack. This risk can be mitigated by only placing the devices in a pairing mode when proximity is detected and also through application-level filtering of the devices. For example, if the radios are neither connectable nor discoverable, except for a few seconds while the pairing information is exchanged, it is extremely unlikely an eavesdropper could detect the Personal Area Network (PAN) and generate a MITM attack before the pairing completes. If an incorrect device pairs, application level software can cause the radio to delete pairing information and destroy the RF connection. Such deletion and destruction can occur before any data are accepted across the RF link. Application level software can determine correct device pairings through several methods including comparing the Bluetooth address to a known list of acceptable addresses, through an application level challenge-response or other authentication solution.

FIG. 1 shows example physiological sensors that can be used on a patient 102 in a personal area network for a medical application. The four physiological sensors include an example thermometer 104, ECG sensor 106, blood pressure sensor 108 and $SPO_2$ sensor 110. The $SPO_2$ sensor is also known as an oxygen saturation sensor. The physiological sensors 104, 106, 108, and 110 can be paired to patient monitor 208 and communicate with a medical application over a personal area network, as described below.

Figure 2:
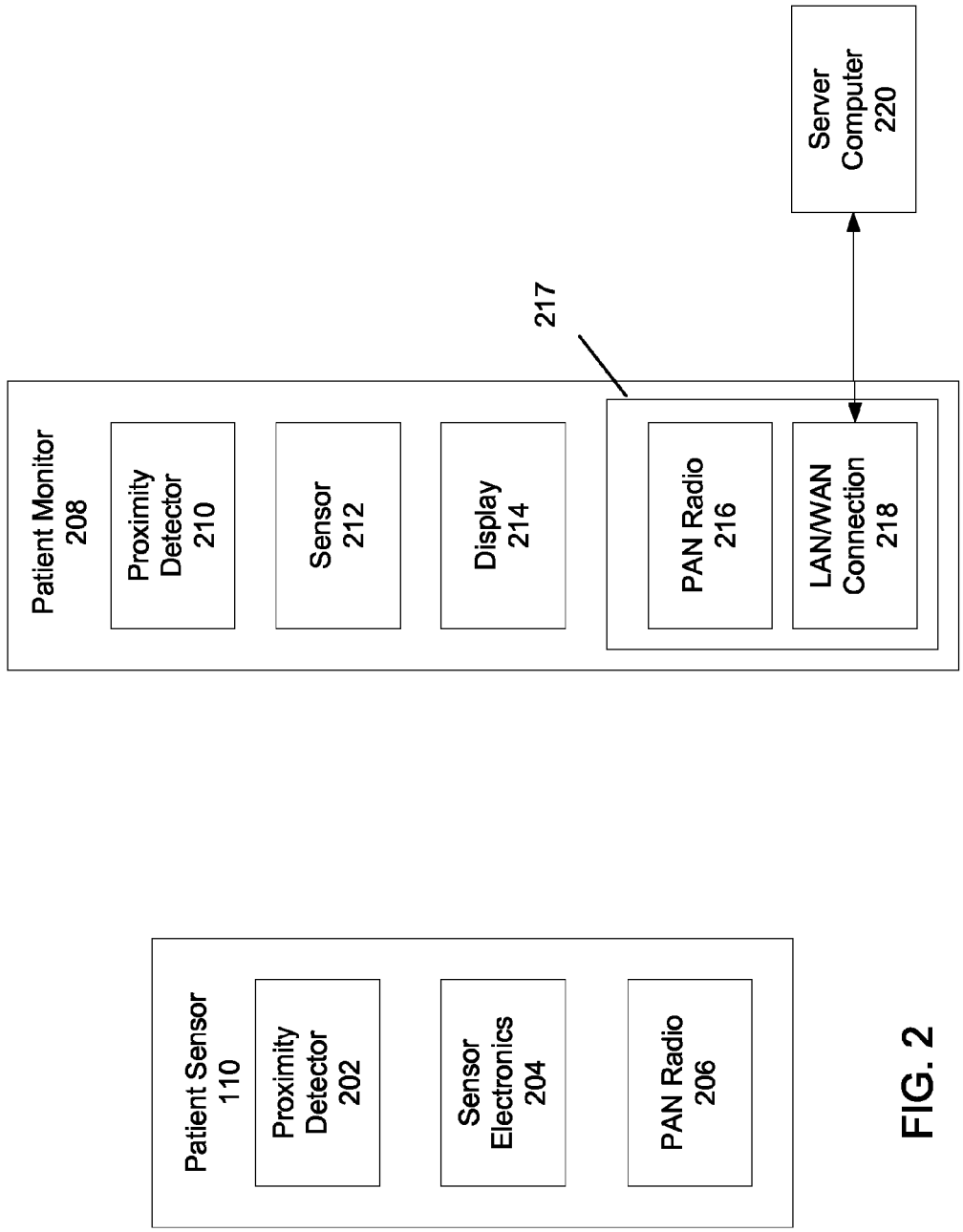
FIG. 2 shows example modules of a physiological sensor and of the patient monitor of FIG. 1.

FIG. 2 shows an example personal area network 200 for a medical application. The example personal area network 200 includes the example $SPO_2$ sensor 110 and an example patient monitor 208. The example personal area network 200 may also include one or more of the example physiological sensors 104, 106 and 108 (shown in FIG. 1). Each of the example physiological sensors 104, 106, 108, 110 has PAN capability. The example $SPO_2$ sensor 110, as well as the example sensors 104, 106 and 108, also includes a proximity detector 202, sensor electronics 204 and a PAN radio 206. The proximity detector 202 may be disposed within the radio 206. For a Bluetooth radio, an approximate proximity detection may be made using signal strength. For an UWB radio, absolute ranging may be possible, allowing not just proximity detection, but also the precise distance between two UWB radios.

The example patient monitor 208 includes a proximity detector 210 and may include one or more embedded sensors 212 that have a physical attachment to patient monitor 208. The patient monitor also includes a display 214 that indicates the state of various sensors and network connections. In addition, the patient monitor 208 includes a PAN radio 216 and a LAN/WAN connection 218, providing a gateway 217. The LAN/WAN connection 218 permits data to be transmitted between the example personal area network 200 and one or more server computers 220 that are accessible via the LAN/WAN connection. Other network connections including mesh, UWB, MAN and the like may allow connection to the one or more server computers 220, patients sensors 210, or other patient monitors 201

Typically, the example physiological sensors 104, 106, 108, 110 are not powered on until they are activated and placed on the patient. The example patient monitor 208 may be continually powered on. For example, the patient monitor 208 may be wall-mounted unit or may be permanently mounted to a stand or other apparatus in hospital room. When the patient monitor 208 is permanently mounted, the patient monitor 208 typically is connected to AC power and is typically continually powered on. Alternatively, the patient monitor 208 may be a portable unit that is operated via battery power. When the patient monitor 208 is a portable unit, the patient monitor is typically powered on manually via a power-on button. However, in examples, a portable patient monitor may also be power on automatically via the proximity detector 210.

Considering a Bluetooth PAN and other radios that have similar connectivity solutions: in order for Bluetooth pairing to occur, Bluetooth devices must be both discoverable and connectable. By using a proximity detector in a Bluetooth device, for example physiological sensor 110, the Bluetooth device may be kept in a low power state to save power until the Bluetooth device is moved into close proximity with a second Bluetooth device, for example patient monitor 208.

In some examples described herein, the physiological sensor 110 is off. In other examples, the physiological sensor 110 can be in a low power state including for example any of the following and combinations thereof: the physiological sensor 110 being completely off, the microprocessor of physiological sensor 110 operating in a low power mode, the radio in physiological sensor 110 being in a low power mode, the radio in physiological sensor 110 being on, but not in a connectable state, or the radio in physiological sensor 110 being off. Regardless of the state of the physiological sensor 110 and its radio, detection of another proximal device causes the physiological sensor 110 and its radio to move to a state where the radio can connect to another device.

Starting from a state where physiological sensor 110 and patient monitor 208 have never had a PAN connection, when the physiological sensor 110 is moved proximally to the patient monitor 208, power is turned on at the physiological sensor 110, power is turned on at the patient monitor 208 if power is not already turned on at the patient monitor 208, the radios on both the physiological sensor 110 and the patient monitor 208 are placed in connectable mode and at least one radio is placed in discoverable mode, and pairing occurs between the physiological sensor 110 and the patient monitor 208. The pairing establishes a wireless connection between the physiological sensor 110 and the patient monitor 208. Note that if sensor 110 and patient monitor 208 have previously paired and bonded, the radios do not need to discover each other. Similarly, if the sensor 110 and patient monitor 208 have been provisioned with the pairing information, perhaps at manufacturing, the radios do not need to discover each other. Once paired to the patient monitor 208, the physiological sensor 110 is placed on the patient 102 and physiological data is sent from the physiological sensor 110 to the patient monitor 208 via the wireless connection. For a body-worn patient monitor 208, pairing may occur after the sensor is placed on the patient 102 and pairing may occur after the patient monitor 208 is placed on the patient 102.

Providing an auxiliary, low power discovery permits the medical device to be selective in the devices with which it might connect. For example, upon detection of an auxiliary discovery signal, the radio may change state to "discoverable" or "discoverable and connectable" for a limited time so that only the opportunity to connect to the wrong device is decreased compared to a device that is always in the "discoverable" or "discoverable and connectable" state. If both sides of the connection have this feature, then the opportunity to connect to the wrong device is further diminished. When one device is AC powered, the radio may be kept in connectable and discoverable mode all the time and rely on the physiological sensor 110 to correctly initiate pairing. However, if the device is always in a connectable and discoverable state, the opportunity is open for either the wrong device or a malevolent device to connect. Alternately, the AC powered device may exit discoverable mode, but stay in connectable mode. This allows another sensor, perhaps one that has lost contact with its primary gateway, to send physiological data via an alternate gateway. Even if this other sensor does not have a patient ID, a unique identifier such as the sensor serial number can be associated to the patient. With this unique identifier, sensor data transmitted via an alternate gateway can be associated with the correct patient ID at the server computer 220. Another case for keeping radios in connectable mode allows re-connections to occur. Once a physiological sensor is communicating with a patient monitor, each will likely keep its radio in connectable mode, but not discoverable mode. This allows the two devices to re-connect if the RF link is broken, but does not allow any other devices to discover the PAN. To keep the network more secure but still allow devices to reconnect, the devices may also exit both discoverable and connectable states after connecting to sensors and upon loss of RF connection move to the connectable state.

As devices connect to different gateways, the status of those devices, including location, need for periodic maintenance, battery status, software revision and the like may be annotated to a server for use by the biomedical engineers and clinicians. After Bluetooth pairing is completed, status and configuration information are transferred between sensor device and gateway device, for example between physiological sensor 110 and patient monitor 208, to verify that both the sensor device and the gateway device are operational and compatible with each other. For example, application software of patient monitor 208 may query physiological sensor 110 to verify that physiological sensor 110 has passed a diagnostics self-test, to verify the strength of a battery on physiological sensor 110, to determine if any component of physiological sensor 110 is in need of repair or due for periodic maintenance, or to determine the status of the RF connection. This status information may be transmitted along with other parameters from the monitor such as its own RF connection strength to the IT network, battery status, and location. These data may be used to trend performance, debug connection issues, or to determine if maintenance is required. In addition to the status information, the sensor provides model and version information. The model and version of the sensor device are compared with the model and version of the gateway device to determine whether the sensor device and gateway device are compatible.

When the sensor device and the gateway device are paired, the sensor device and the gateway device are said to have a logical connection with each other that is analogous to the connection that occurs when a cable is plugged into the monitor. This logical connection may occur at an RF level or at an application level. For example, the logical connection may occur at the RF level after the devices are paired or the logical connection may occur at the application level when the compatibility check between devices is completed. In the cable analogy, plugging the cable into the device is analogous to the RF connection and the device recognizing the cable and the sensors at the end of that cable are analogous to a connection at the application level.

After status and compatibility are checked and verified between sensor and gateway devices, a clinician may be required to verify the sensor device for a specific patient requiring the clinician to confirm the sensor device for a specific patient provides an additional level of security to ensure that the sensor device is placed on the correct person. In addition, the clinician must confirm the sensor for a specific patient within a short time period after the sensor device and the gateway device are placed in connectable and discoverable modes. Through confirming the device the clinician indicates to the system that the data from the new sensor belongs to the same patient as is indicated on the patient monitor. If the clinician does not confirm the sensor for a specific patient within the short time period, the wireless connection between the sensor device and the gateway device is broken and the logical connection between the sensor device and the gateway device is destroyed. The reset of the logical connection might include removal of the pairing information. By allowing pairing for only a short time period after the sensor device and the gateway device are placed in connectable and discoverable modes, MITM attacks are minimized. The time period must last long enough for both radios to enter the connectable state and connect or to enter the connectable and discoverable state, be discovered, and connect. A short time period may be range from a hundred milliseconds to several seconds. Preferably, the radio exits the connectable state or the connectable and discoverable state immediately upon initiation of a radio connection. Leaving the logical connection in place could allow the sensor to maintain a connection to the incorrect monitor. The system may be configured to allow the unconfirmed connection to remain; but without indicating the patient ID. In this case, a pseudo-ID may be used to identify the data until such time as a patient ID is assigned to the sensor. For example, the data might be saved in a database keyed by the sensor serial number instead of the patient ID. If the sensor is later correctly connected to the proper patient monitor, the data that has been thus far collected and stored is annotated with the patient ID associated with the proper patient monitor. In a solution with proximity detection that supports ranging, the system may have a set of rules that determine when the clinician is required to confirm the sensor device for a specific patient. For example, if a ranging solution has 25-cm range resolution and one gateway is detected within a range of 1 meter and no other gateways are detected within a range of 3 meters, it is likely that the sensor is intended to connect to the gateway within a 1-meter range. The rules may dictate cases where a clinical confirmation is required, for example if two gateways are within a 1-meter range. The rules may present to the clinician a list of gateways from which to select for connection, based on range to the gateways. This latter case provides the clinician a short list of likely gateways (and hence patients) from which to choose.

After the clinician confirms the sensor device for a specific patient, the clinician selects a connection mode for the connection between the sensor device and the gateway. The connection mode describes the extent to which alarms and equipment alerts are generated in the connection. An alarm refers to an error condition for a patient while an equipment alert refers to an error condition for the medical equipment. Application software at the gateway device permits the clinician to assign one of three connection modes—loose pairing, tight pairing and locked. Each connection mode is defined to match a specific workflow and provides a class of alarm response. For example, loose pairing provides one class of alarm response, tight pairing provides a second class of alarm response and locked provides a third class of alarm response. Other application-level connection modes and combinations thereof may be used to match different workflows.

Loose pairing is typically used for a spot monitoring workflow in which a sensor device is periodically brought into a patient's room to check a physiological parameter that is not being monitored by the patient monitor in the patient's room. This is sometimes referred to as spot checking. In a workflow that uses loose pairing, there are no equipment alerts if the connection between the sensor device and the gateway device is broken. There may also be no alarms as the workflow includes a clinician at the patient location.

Tight pairing is typically used for a workflow in which there is continuous monitoring of patient physiological data. In a tight pairing connection, an equipment alert is generated whenever certain error conditions occur. For example, an equipment alert is generated when the wireless connection between the sensor device and the gateway device is broken. This is analogous to an equipment alert if an ECG cable is removed from the monitor or the ECG electrode falls off the patient. Another error condition that causes an alarm to be generated is when the gateway device determines that one or more physiological parameters received from the sensor device is above or below a predetermined threshold. Other error conditions that cause an equipment alert condition to be generated include: need for maintenance (including scheduled periodic maintenance), sensor device loss of power, unacceptable RF performance such as high packet loss or poor signal level, RF interference, inappropriately sized blood pressure cuff detected, ECG lead failure, SPO$_2$ sensor with no signal detected, a sensor that is not confirmed for a particular patient, and other equipment alerts familiar to those skilled in the art.

When an error condition occurs in the tight pairing connection mode where the connection from the patient to the device comes into question, in addition to an alarm being generated, the wireless connection between the sensor device and the gateway device may be broken and pairing information for the connection may be deleted at the sensor device and at the gateway device. For example, if a physiological sensor falls off the patient, when the physiological sensor is re-attached, the clinician may be required again connect the Bluetooth radios. The deletion of pairing information when the connection is broken prevents physiological data from the sensor device from being associated with an erroneous patient identification number. Alternately, the application level software may allow the Bluetooth connection to persist, but stop annotation of the data with the patient ID until the patient ID is confirmed. A system may also stop the data flow from the sensor until the patient ID is confirmed. Patient ID may be confirmed through many means, including a clinician making a confirmation step, absolute range to a gateway, absolute range to other physiological sensors, or correlation of physiological signals. The system may present a menu for the clinician to confirm the sensor for the patient. The system may assume that if the range to the gateway is less than a predetermined threshold, the system may confirm the sensor for the patient with no clinician action. The pre-determined threshold is configurable to meet the needs of various workflows. The system may have a record of the data and use an algorithm such as pattern recognition to verify the sensor is still attached to the same patient or the system may correlate the physiological signal from the unconfirmed sensor with physiological data from a confirmed sensor to determine if they are still on the same patient. If the data correlates, the system may begin annotating data from the previously unconfirmed sensor.

Locked pairing is used when it is determined that a sensor device is only to be connected to a specific gateway device, for example to the patient monitor 208 or to a select set of gateway devices. A monitor on a roll stand with wireless sensors is an application where locked pairing may be useful. When a sensor device is used with locked pairing, an equipment theft alert is generated when an attempt is made to connect the sensor device to a gateway device that is not included in the select set of gateway devices. The intent of a locked connection is to minimize the potential for the sensor device from being moved, borrowed or stolen from the gateway device to which the sensor device is connected. To allow the locked sensor device to be moved to a different gateway, as may be the case when the original gateway is damaged or has a dead battery, a reset capability is designed into the product. This may be through a hidden service screen, a reset button, through a specific set of key strokes or similar method that obscures the ability to remove the locked pairing configuration.

The present disclosure is also directed to example systems and methods for using a ranging feature of the proximity detector to determine whether to add the sensor device to a PAN. Once a sensor device is joined to a PAN and a gateway in the PAN has patient context, the system may assume that all data from sensors in the PAN is to be associated with the same patient. This gateway is the patient's primary gateway. Data transmitted to the primary gateway will be recorded in the patient's medical record. However, in some cases it may be that sensors lose connection to the primary gateway. The sensors may safely maintain the patient context while continuously attached to the patient. This continuous attachment can be determined if the sensor is continuously making a physiological measurement, through a skin contact sensor, or similar means. Sensors that lose connection to a primary gateway may uplink data via an alternate gateway if the sensors have the patient context, e.g. patient identifier, (PID) and transmit it with the data via the alternate gateway or if the alternate gateway has the patient context. For an alternate gateway to obtain the patient context, the primary gateway may transmit the sensor's unique ID, e.g., MAC address, and the patient context, e.g., PID, to all other gateways in range. Then, the alternate gateway can associate the physiological data received from the sensor with the Patient ID: when a sensor joins an alternate gateway, the alternate gateway associates the physiological data with the sensor's unique ID and associates the sensor's unique ID to the patient ID. Another way to support roaming is for all sensors to transmit a unique ID with the patient data and have a system database that stores the mapping between unique ID and patient ID. When a sensor joins a primary gateway, the primary gateway receives the sensor's unique ID and sends the sensor's unique ID along with the patient ID to the system database. When a sensor moves to an alternate gateway, the system may associate the patient ID to the received physiological data based on the sensor's unique ID. This pseudo-PID may be used if the system knows a unique serial numbered sensor is associated with patient ID. In this case, the sensor can transmit its serial number and the data via an alternate gateway and the system can lookup the PID based on the serial number. In addition, when the sensor device is added to the PAN, the systems and methods provide for transferring patient context, typically in the form of a patient identifier (patient ID), to the sensor device. Other examples of patient context are a room number, clinician, date of birth, gender, and patient history. Pseudo patient ID may also be any unique number, e.g. a serial number or MAC address, when a database maps that unique number to a patient identifiable datum such as patient ID. Other examples of patient context and of pseudo patient IDs are possible. In the case of using a pseudo patient ID, the pseudo ID would be transmitted to the gateway after the sensor joins the PAN, allowing the system to associate patient context via the pseudo patient ID. The systems and methods provide for transferring patient context from the sensor device along with any physiological data that is transferred from the sensor device. Transferring patient context along with physiological data helps ensure that physiological data from the sensor device is correctly identified, particularly in the case where the patient's sensors are out of range of the patient's primary gateway (one that has the patient context) and upload the data via a different gateway. In some workflows, for example taking patient vitals in a triage setting, there is no need to maintain patient context for a long duration nor across multiple gateway and in these cases, patient context may only exist in the primary gateway.

The ranging feature of the proximity detector makes uses of UWB to determine the distance between the sensor device and other devices with compatible UWB transceivers. For example, a sensor may determine the distance between itself and a patient monitor on the PAN with an UWB transceiver, for example patient monitor 208. The sensor may also determine the distance between itself and at least one other sensor with an UWB transceiver. Based on the distance between the sensor device and the at least one other sensor device or the distance between the sensor device and patient monitor 208, a rules engine determines whether the sensor device may be added to the PAN. Typically, the ranging feature provides for accurately determining distances as close as 10 cm and continues to operate as long as the two radios maintain a communication link. For a radio operating in a PAN, this range is typically on order of 10 m, with approximately 10 cm resolution. For radios operating with higher signal to noise rations, the maximum range increases and ranging resolution improves. The sensor device to be added to the PAN, for example an SPO2 sensor, is typically brought into a hospital room by a clinician. The SPO2 sensor typically sends out ranging signals and the frequency of ranging signals may be traded off against power consumption. Typically, a ranging response must be under 1 second or the user detects a lag in the system response. As a result of exchanging ranging signals, the SPO2 sensor determines the distance between the SPO2 sensor and the one other sensor device or the distance between the SPO2 sensor and patient monitor 208. When the distance between the SPO2 sensor and the one other sensor device or the distance between the SPO2 sensor and patient monitor 208 is within a predetermined threshold, a determination is made to add the SPO2 sensor to the PAN. The predetermined threshold is stored on the SPO2 sensor and may be configurable. A typical threshold is 25 cm, and other thresholds are possible. For example, if a hospital ward has a standard room layout, the threshold may be the distance from the door in the patient room to the patient monitor 208 in that same room. When the SPO2 sensor is powered on, the SPO2 sensor may immediately begin sending ranging signals. The rate of sending ranging signals may change over time, for example, high at turn on and high immediately after detecting another device is within a range of perhaps 5-meters, but low at other times to save power.

When it is determined that the SPO2 sensor is to be added to the PAN, the SPO2 sensor is first identified and authenticated. With a ranging technology such as UWB, a range requirement may be implemented as part of authentication between sensor devices. The system may be configured to transmit authentication information over the primary channel when the range is within a certain value. The system may be configured to require no authentication except determination that the range is within a certain value. In this case, ranging would be considered authentication using an OOB channel. When the ranging occurs simultaneous to the data transmission, a man-in-the-middle attack is mitigated as this sort of attack would result in transmissions from a range that exceeds a predetermined distance. The system may also be configured to use an OOB channel for transmitting authentication credentials such as MAC address and link key. Authenticating the SPO2 sensor (and other sensor devices) when the SPO2 sensor distance is within the predetermined threshold helps minimize MITM attacks.

Out-of-band communication may use one or several mechanisms, for example, infrared, ultrasonic, magnetic, Wi-Fi, etc. As an example of out-of-band authentication using a magnetic means, the coil of the proximity detector in the SPO2 sensor may be used to transmit the MAC address. The MAC address may be transmitted by pulsing current through the coil in the SPO2 sensor on and off thereby modulating the MAC address onto the current. The modulated pulsed current from the SPO2 sensor is detected and demodulated by a coil in the one other sensor device or gateway device already on the PAN. Similarly, the two sides can generate and then share (or compare) a link key across the OOB link. Various types of modulation can be used, including amplitude modulation and phase modulation. For example, amplitude modulation may be implemented by varying the amount of current that is pulsed in the coil. A small amount of current produces small pulses and a large amount of current produces large pulses. Other methods of in-band and out-of-band authentication are possible.

Once the SPO2 sensor is authenticated, a determination is made as to whether the SPO2 sensor is to inherit the patient context of the PAN. The determination is needed to ensure that patient context is transmitted to the correct sensor device. It may be that once range-based authentication occurs, patient context is automatically communicated to the sensor device. Range-based authentication may be either uni-directional or bi-directional. In uni-directectional, range-based authentication, only one device needs to determine whether it is within a pre-determined range threshold. In bi-directional, range-based authentication, each device measures the distance to the other and each device determines whether it is within a pre-determined range threshold of the other device before authentication is complete.

When making a determination as to whether another device such as the SPO2 sensor is to inherit the patient context of the PAN, several factors may be considered. One factor is the distance between devices (for example the distance between the SPO2 sensor and the one other sensor device on the body of the patient, already part of the PAN). A second factor is a time interval that the distance between devices is within the predetermined threshold. The time interval is considered because devices may come into close range for many reasons. For example, clinicians may have a sensor device in their pocket at the time that the clinician comes in close contact with the patient. The clinician may briefly come in close enough contact with the patient that the sensor device in the clinician's pocket may be within the predetermined threshold. However, in this case the sensor device in the clinician's pocket is not meant to join the PAN. However, if the clinician puts the sensor device on the patient, it is a better indication that the sensor device from the clinician's pocket is to be part of the PAN. By considering the time interval that one sensor device is in close proximity to another sensor device, a more accurate determination can be made as to whether the sensor device should join the PAN. An alternate solution is to allow the sensor to join the PAN with the second factor of time interval set to 0. In this case, the sensor would join the network, but when the clinician leaves the patient proximity with the sensor, the rules engine removes the patient information because it exceeded a predetermined range threshold without ever have made a physiological measurement. A clinical use case may indicate that a smart phone, PDA, tablet or similar device the clinician carries is to join the PAN to learn the patient context, allowing an application on the smart phone to automatically call up germane forms, documents, or data for that patient. For example, when a smart phone learns the patient ID, the smart phone may automatically present a form for display and entry of vital signs measurements when the user of the smart phone has the role of recording vital sign measurements. Alternately, the application might start an electronic health record (EHR) application, such as Care360™ or AdvancedMD™. When a sensor on the PAN makes a reading and transmits it, the reading is communicated to the EHR application, typically via an application program interface (API). If the user of the smart phone has the role of diagnosis (e.g., physician), then the application might call a different view of the EHR or form, for example physical exam notes, recent lab results, ECG or EEG waveforms, x-rays, or similar relevant data. Since the smart phone likely doesn't have the resolution to display an x-ray, the smart phone may work through the network to discover a local display and cause the image to display on that local display. These examples of using proximity/ranging along with the clinical use case allow software to present appropriate information to the caregiver.

A third example factor is whether the sensor device has made a physiological measurement, particularly if the sensor device has made a measurement within a range of a predetermined threshold. For example, if the sensor device is an SPO2 sensor and one or more SPO2 readings have been taken from the sensor device, it is a good indication that the sensor device should join the PAN for the patient. Other example factors may be considered.

In examples, the rules engine determines whether a sensor device is permitted to join a PAN and whether patient context is to be transferred to the sensor device. The rules engine evaluates one or more of the factors discussed in order to make this determination. In addition, the rules engine may evaluate other factors. The authentication step used to determine that patient context is to be transferred to the new device, typically includes use of an out-of-band channel, e.g., determining range. The patient context may also be transmitted over an OOB channel. Even if patient context is not transmitted to the sensor device, with the sensor validated as a member of the PAN, the sensor can transmit data to the patient monitor, where the data and patient ID are associated. Data may be subsequently transmitted to the EHR/EMR.

Transferring patient context to the sensor device via an OOB channel is similar to authentication via the OOB channel. The patient context comprises an identifier for the patient, typically a Patient IDentification number (PID). The OOB channel may be a magnetic channel, as discussed for authentication or it may be another type of OOB channel, such as IR, ultrasound, wi-fi, using an NFC standard, UWB, etc. In examples, once the sensor device is authenticated and a determination is made to transfer patient context to the sensor device, the patient context for the sensor device is obtained from the patient monitor 208. The patient monitor 208 typically stores patient context so that the patient context can be displayed on a display screen of the patient monitor 208. In cases where the patient context is not stored on the patient monitor 208, the patient monitor 208 may obtain the patient context from the EMR/EHR system via gateway 218, from the ADT (admit discharge transfer) system via gateway 218, or by clinician entry of the information. Once the patient monitor 208 obtains the patient context, the patient monitor 208 transfers the patient context to the sensor device using either the OOB channel or authenticated primary communication channel. The patient context is then stored on the sensor device. Transferring patient context by these means helps ensure that the personally identifiable information (PII) is securely transmitted, particularly in the case where a secure link on the primary channel cannot be created.

Some sensor devices, for example a thermometer, have limited memory and are not able to store patient context information. When a sensor device is unable to store patient context, a serial number for the sensor device may be correlated with patient context. The serial number in effect becomes a pseudo patient ID. In examples, the serial number may be the global identifier sent to the patient monitor 208 during the authentication process. When temperature data is subsequently transmitted from the thermometer to the patient monitor 208, the serial number is transmitted along with the temperature data. When the patient monitor 208 receives the temperature data and serial number, the patient monitor 208 looks up the patient context from the serial number and identifies the patient for which the temperature data is transmitted. Once the patient context has been identified for the temperature data, the patient monitor 208 is able to send the temperature data and the patient context to the EMR/EHR system.

The radio on the sensor device typically is programmed with a default configuration, including such parameters as the predetermined threshold for ranging. The default configuration may be updated in real-time without requiring a reset of the sensor device.

The sensor device may determine ranging information based solely on components included with the radio. Ultra-wide band components are included in the sensor device. No add-on accessories or software are needed as is the case in typical Wi-Fi location solutions. Bluetooth and Wi-Fi solutions both lack the ability to perform precise ranging.

The time duration for which patient context is stored on the sensor device is dependent upon a clinical workflow. Different workflows may be used for a patient in a medical setting. Some example clinical workflows are continuous monitoring and spot monitoring. Within these workflows, sensors may have monogamous and polygamous connection profiles. Other example workflows may be used. With a continuous workflow, sensor data is obtained from the patient and transmitted to the patient monitor 208 on an ongoing and continual basis. For a continuous workflow, patient context remains stored on the sensor device even when the primary gateway is not available. When the patient ambulates with the wireless sensor devices, the wireless sensor devices can connect to any hub or gateway to upload data. Because the wireless sensor has the patient context, it can transmit the patient context with the data, allowing the end receiver to unambiguously match the data with the correct patient record. With a spot workflow, sensor data may be obtained from the patient on a periodic basis, for example whenever a clinician enters a room and takes vital signs for the patient. With a spot workflow, sensor devices may be periodically added on the body of a patient and periodically removed from a patient. When a sensor device is permanently removed from a patient, any stored patient context on the sensor device also needs to be removed from the sensor device. With a monogamous connection profile the sensor is provisioned to connect to exactly one other device. When the sensor turns on, the sensor attempts to connect to only that one device. This connection profile is useful when, for example, a sensor is to stay in the same room and connect to the patient monitor in that room. This profile is not agile, and once provisioned, it is understood that the patient context of the patient monitor and the patient context of the sensor will be the same. When a new patient is brought to the room, the patient context of the patient monitor is updated to match the new patient. With a polygamous connection profile, the sensor is provisioned to connect to any member of a set of other devices. For example all thermometers on a hospital unit may be provisioned to connect to any patient monitor deployed on that unit. The polygamous connection profile is agile, but requires additional confirmation steps such as a clinician's confirmation of a patient context change or specific rules indicating the ranges at which a sensor should abandon a first patient context and at which a sensor should acquire a new patient context. The polygamous connection profile is useful when, for example, a hospital unit has multiple sensor devices such as thermometers and a clinician may use any thermometer in any room. Here, the thermometer would require the clinician to either enter the patient context, indicate which patient monitor the thermometer should upload data to, or depend on a rules engine with pre-determined ranges for breaking/ making patient context changes. Using the rules engine, the thermometer might connect to a monitor that is within a range of 1-m. If the thermometer detects multiple monitors within approximately 1-m range, for example 1.2 and 1 meter, then the rules engine may query the clinician to confirm the monitor rather than making an automatic confirmation. The ranges and rules are determined by the clinical work flow and physical setup in a given environment. During provisioning, the sensor device is programmed with the clinical profile (including connection) parameters. For example, a thermometer may be provisioned for spot monitoring and a polygamous connection profile as follows:

When the sensor device is within 1 meter of a patient monitor and there is no current connection to a monitor, the sensor device attempts to connect to that patient monitor.

Moving more than 5-m from the connected monitor results in a disconnect and removal of any existing PID.

As long as no other patient monitor is within the 1 meter range and the current monitor is within a 5 meter range, the sensor device stays connected for 5 minutes, with the connection timer reset each time a physiological measurement is made.

If another patient monitor is within the 1 meter range, the current monitor is within the 5 meter range, and the time has not expired, a request is annunciated to confirm a change of patient monitor.

When connecting to a new patient monitor, the system associates the thermometer data with the patient context of the new patient monitor.

With the polygamous connection profile, a clinician making multiple temperature measurements in a first room stays connected, but upon a room change, the first patient context and connection to the first patient monitor are cleared. For another sensor device, such as EKG, a rule may be to remove the patient context and patient monitor connection when the sensor device is removed from the patient. However, this might cause the patient context to be lost when EKG electrodes are changed. Additional rules may be added to the connection profile such as removing patient context from the sensor device when the distance between the sensor device and another connected device on the patient is greater than a predetermined threshold and when a time that the distance is greater than the predetermined interval is more than a predetermined time interval. For some workflows, a patient may be confined to one location, for example a hospital bed, for an extended period of time. For other workflows, a patient may be ambulatory and move around their room or a hospital floor. During a workflow in which a patient is ambulatory, it may be desirable to monitor the location of the sensor device and to change the patient monitor device or gateway that receives data from the patient device to a patient monitor device or gateway that is closer to the sensor device. As the patient moves around the hospital the ranging mechanism on the sensor device may determine that the sensor device is moving out of the range of the patient monitor 208 and is now closer to a different gateway device. As the sensor device moves out of the range of the patient monitor 208 and comes into the range of another gateway device, the sensor device may transmit sensor data to the gateway device that is now in range. However, because the sensor device has the patient context, the gateway device correctly identifies the data as belonging to the patient.

When determining which gateway to connect to, the sensor device may use other metrics in addition to distance. Some examples of additional metrics include signal strength, noise level on a floor, interference level, retry rate, the number of devices already connected to a particular gateway, etc. Other examples are possible. In addition, the sensor device may be configured to connect to a specific gateway when multiple gateways are at the same distance from the sensor device.

When a determination is made whether to switch gateways, it may be desirable to determine an absolute location of the sensor device. In a hospital setting, the location of each fixed gateway device and patient monitor is typically known. When a sensor device is moved to be in close proximity with a gateway device, once it is determined that the sensor device is within close proximity (at a range, r) of the gateway device, because the location of the gateway device is known, the location of the sensor device is also known to be on a sphere of radius r with center at the location of the gateway. If r is small, perhaps less than 25 cm, it can be assumed that the sensor and the gateway are co-located. There may cases where the sensor device is within range of more than one gateway device. When the sensor device is within range of more than one gateway, a method of interpolation, for example triangulation, may be used to determine a more precise location of the sensor device. For example, if the sensor device is within range of three gateway devices, the location of each of the three gateway devices may be considered as a point on a triangle. Using triangulation, the center of the triangle may be determined and established as the absolute location of the sensor device. Once the absolute location of sensors is known, the sensors themselves may be used to triangulate the location of yet additional sensors.

Gateways may transmit to back-end server ranges and/or locations of sensor devices that are connected and sensor devices that are detected, but not connected, for the purpose of location. Knowing the location of a sensor device, and hence the location of the patient permits alarms to be escalated to the closest clinician and provides alerts if the patient moves out of a designated area. In addition, knowledge of sensor location permits sensors to be located when lost and permits alerts if sensors are moved out of a specific area. When periodic maintenance is required on a group of devices, a biomedical engineer may query the back-end server for the last-known location of devices. As a theft deterrent, sensors may be automatically disabled when the sensor location is not within certain parameters, such as a particular area of a hospital. As a second theft deterrent, the sensor may be automatically disabled except when making an initial connection to a particular gateway. This would allow the sensor assigned to a particular room to connect to the gateway in that room, and then roam as the patient ambulates. However, if the sensor has not made a reading recently, it will only connect to its particular gateway.

When communicating status and control information between the sensor device and gateway device, the radios on the sensor device and gateway device preferably implement a method to transmit status and control information and physiological data without needing to switch operating modes. The method is implemented by via an application programming interface (API) on the sensor and gateway devices. Examples of status and control information include signal strength, current network status, authentication status, changes to alarm thresholds, charging status, over- and under-voltage detection, and battery charge level. Other examples of status and control information are possible.

Ranging information may also be used to respond to queries. For example, a sensor device may receive a query when a connection process is started (i.e., when the sensor device is within a predetermined distance of another sensor device or the patient monitor). The query may be issued to indicate that the connection process has been started and to confirm that the connection process should be completed. The sensor device may respond to the query by moving the sensor device closer to or farther away from the other sensor device or the patient monitor. A movement of the sensor device toward the other sensor device or patient monitor may be interpreted as a "yes" and a movement away from the sensor device or patient monitor may be interpreted as a "no". In other examples, a "no" may represent movement toward the other sensor device or the patient monitor and a "yes" may represent movement away from the other sensor device or the patient monitor.

Alternatively, an accelerometer may be used to detect motion corresponding to a "yes" or a "no". For example, movement of the sensor device up and down may constitute a "yes" and movement of the sensor device from side to side may constitute a "no". In other examples, movement of the sensor device up and down may constitute a "no" and movement side to side may constitute a "yes". Moving the sensor device slowly may constitute a "no" and moving the sensor device rapidly may constitute a "yes"

As another example of the use of ranging motion to respond to queries, a clinician may use sensor motion to indicate whether a temperature reading is correct. Sometimes there may be an error in a temperature reading obtained via a thermometer. Through a certain motion, per the examples above, a clinician can confirm that the temperature reading is correct and have the temperature reading transmitted to an EMR/EHR system or cause the reading to be deleted.

Ranging information may be used to detect relative motion between two medical devices as the range increases or decreases. Detection of motion can cause a state change of the medical device and/or the radio. Since ranging requires power, it is advantageous to minimize use of the ranging function for battery-operated devices; however, minimizing use of the ranging function may cause a lag in response time. An adaptive ranging function that determines range perhaps every 1 second could determine when the sensor is being moved and then change the ranging rate to every 0.1 seconds, for example, to provide fast response and ability to detect finer motion. When the ranging function determines the sensor is within a certain range of another sensor or medical device, it may cause the radio state to change from discoverable state to connectable and it may move the radio from a standby (ranging only) to a fully-on state to allow the connection to be made. When a first sensor's radio determines it is within a certain range of a second sensor, an output from the first sensor's radio may cause the first sensor to move from a standby or off state to a fully on state. Ranging values may be averaged for higher accuracy.

In some embodiments as explained later, the radio on the sensor device may operate in a low-power mode. In these embodiments, the proximity detection feature of the radio may be used to turn on a sensor device when another sensor device, for example the SPO2 sensor, or gateway comes into close proximity or when certain criteria are met. For example, the radio may turn on the sensor device, putting the sensor device in a connectable state, when a MAC address matches. Other criteria may include detecting a specific device profile and through action such as an accelerometer, physical contact and detection of a magnet or a magnetic field produced by a coil carrying a current. Upon initial power-up, the radio may go immediately into a first mode to quickly detect devices and then go into a lower-power mode. In the lower-power mode, the sensor device may detect other devices or may be detected by other devices, although not as rapidly as during initial power-up.

The API on the sensor and gateway devices also permits configuration of the radio on the sensor and gateway devices to configure the radio to sleep and to awaken the radio when a sensor or gateway device is ready to transmit data. For some sensor devices, the radio may remain in a sleep mode until an alarm occurs. The alarm may be related to a proximity detection beacon or to a wake-up check message requesting status from the radio. When the alarm occurs, the radio awakens to process the alarm. The API may also allow configuration to optimize channel robustness vs. power. For example, in a 54 Mbps channel, 3 Mbps requires the transmitter to only have a 5.5% duty cycle; however, there may be a 17 dB improvement in receiver sensitivity at 6 Mbps vs. 54 Mbps.

As noted, the sensor devices used in the PAN are wireless devices. Because wireless devices are inherently less reliable than wired devices, the radio on the sensor devices incorporate forward error correction or other means to recover packets that are received without transmission errors.

In example embodiments, the sensor devices in a PAN may all be in the range of a hub device such as patient monitor 208. In these embodiments, when one sensor device detects a radio of a sensor device not already on the PAN, the sensor device communicates the detection of the sensor device to the other sensor devices on the PAN and to the patient monitor. As a result, the patient monitor moves to a state in which detection and connection can occur rapidly.

In example embodiments, the ranging capability of the sensor device may also support a scatternet. A scatternet is a network that comprises two or more personal area networks, each personal area network having two or more RF enabled devices. In a scatternet, at least one of the RF enabled devices is a member of two PANs, allowing communication between PANs. In a BT scatternet, this device is a slave in one PAN and a master in another. In a scatternet, there is an intersection of personal area networks such that one slave Bluetooth enabled device is part of each of two intersecting personal area networks. With UWB ranging, RF-enabled devices in the scatternet may connect to each other securely using range-based authentication.

Figure 3:
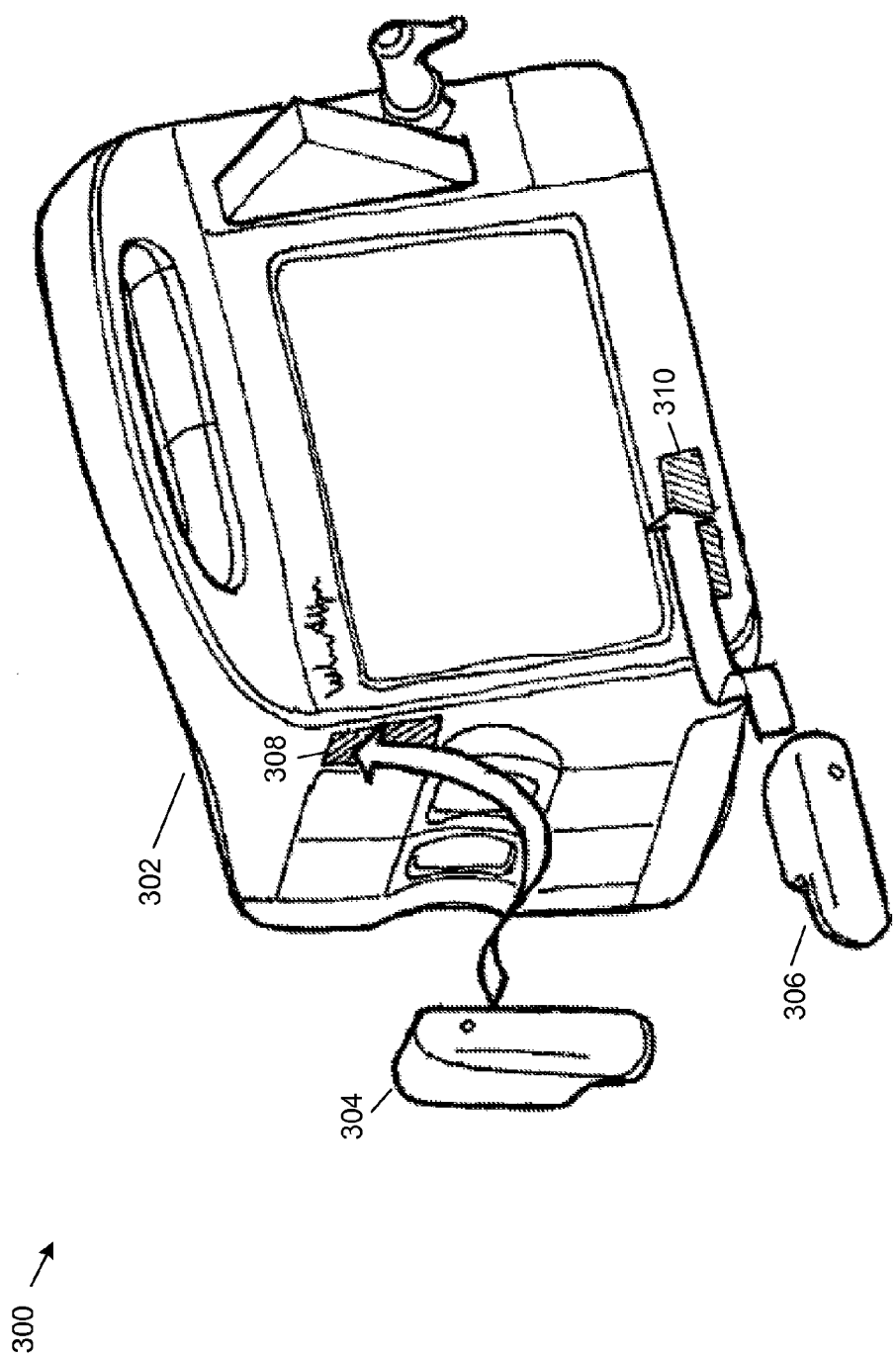
FIG. 3 shows an example patient monitor that includes a proximity detector.

FIG. 3 show an example patient monitor 300. The example patient monitor 300 is a portable device and includes two example proximity detectors 308 and 310. The proximity detectors 308 and 310 are mounted internally in the patient monitor 300 with one surface of each of proximity detectors 308 and 310 being adjacent to an external surface of the patient monitor 300.

Also shown in FIG. 3 are two example physiological sensor devices 304, 306, each including a proximity detector, possibly disposed as part of the radio. Physiological sensor devices 304, 306 are both proximal to the proximity detector 308 disposed in patient monitor 302 and may both join the patient monitor PAN using range-based authentication. In examples, more or fewer proximity detectors may be used and the proximity detectors may be located on different areas of the patient monitor 300, or as an external device, perhaps connected via USB to the patient monitor.

Figure 4:
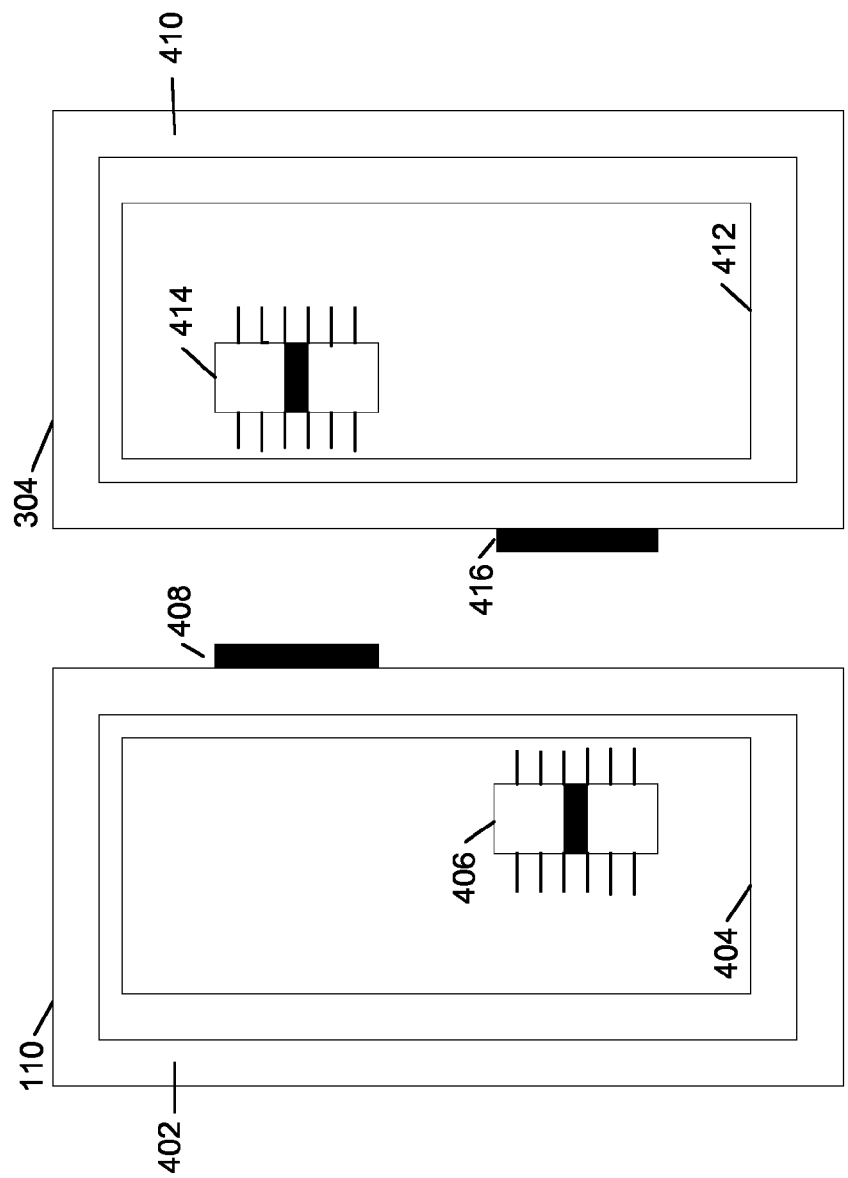
FIG. 4 shows example components of the proximity detector of FIG. 3.

FIG. 4 shows an example physical view for the proximity detection mechanism for physiological sensor 110 and proximity detector 202 that is separate from the radio. Physiological sensor 110 is housed in a plastic housing 402 and includes a printed circuit board (PCB) 404 that includes sensor electronics 204 and Bluetooth radio 206 (not shown), a magnet 408 and a magnetic detector 406. The magnet 408 and magnetic detector 406 comprise proximity detector 202. Patient monitor 208 is housed in a plastic housing 410 and includes a printed circuit board 412, a magnet 416 and a magnetic detector 414. The magnet 416 and magnetic detector 414 comprise proximity detector 210. Patient monitor 208 includes the Bluetooth radio 216 (not shown). When physiological sensor 110 is moved into close proximity with patient monitor 208, magnet 408 on physiological sensor 110 activates magnetic detector 414 in patient monitor 208 and magnet 416 on patient monitor 208 activates magnetic detector 406 on physiological sensor 110.

The magnetic detectors 406, 414 are typically a magnetic switch such as a reed switch, a reed relay, a Hall Effect sensor, a Hall Effect switch or a giant magnetoresistance (GMR) detector. These magnetic switches permit proximity detection using very low power.

The reed switch is a normally open switch, thereby drawing little or no power in the open state. The reed switch closes when a magnetic field of a predetermined threshold is detected by the reed switch. A typical threshold for a sensitive reed switch may vary between 5 Ampere-Turns and 15 Ampere-Turns. However, this assumes a uniform magnetic field along the axis of the axially leaded part.

A Hall effect sensor generates a voltage in response to a magnetic field. The generated voltage increases as the magnetic field increases. For example, when a magnet is moved in the proximity of the Hall effect sensor, the magnetic field of the magnet cutting through the sensor increases as the magnet is moved closer to the Hall effect sensor. The Hall effect sensor may be combined with circuitry such as a comparator that permits the Hall effect sensor to act as a switch. When the magnetic field reaches a predetermined threshold, a magnetic switch closes, signifying an "on" state. A sensitive Hall effect sensor may operate at field strengths of around 10 to 25 Gauss, depending on temperature and frequency of the magnetic field.

A GMR switch includes giant magnetoresistance material and makes use of the concept of magnetoresistance. With magnetoresistance the electrical resistance of the GMR material changes its value when a magnetic field is applied to it. When the magnetic field reaches a predetermined threshold, the resistance of the GMR material is changed to a point such that sufficient current flows through a bridge in the GMR switch to close the GMR switch, signifying an "on" state. Some GMR switches, for example GMR switches in the AFL200 series from NVE Corporation, require only a few microamperes of supply current. A sensitive GMR switch may operate at a field strength of 7-13 Gauss.

Whether the magnetic switch is normally open or normally closed is not relevant to the detection of an applied magnetic field; rather only the state change is important.

Magnetic flux densities decrease in strength exponentially with increasing distance from the source of the magnetic field, for example a magnet. The magnet 408 must be strong enough to activate magnetic detector 414 when physiological sensor 110 is brought in the proximity of the magnetic detector 414. However, at the same time, the magnet 408 must be positioned so that the magnet 408 does not falsely trigger magnetic detector 406 or any other magnetic detectors in other medical devices that may be implanted on a patient. For example, implantable cardio defibrillators may have embedded magnetic detectors that are typically activated at a field strength of greater than 10 Gauss. However, in order to create a magnetic field that is reliably detectable by magnetic detector on a patient monitor 208, magnet 408 and magnet 416 may need to provide a magnetic field or more than 10 Gauss.

Each magnet 408, 416 is located on the outside of their respective plastic housing 402, 410. Each magnet 408, 416 is recessed in the plastic housing 402 and positioned so that one side of each magnet 408, 416 is flush with a side of the plastic housing 402. The reason magnets 408 and 416 are located on the outside on their respective plastic housing 402, 410 is to permit the use of a weaker magnet than would be needed if the magnets 408 and 416 were located within their plastic housing. The reason for this is the exponential decrease in magnetic flux density with distance. Suppose a magnet were placed on the inside of the plastic and had sufficient magnetization to create a field of 10 Gauss at 4 mm outside the plastic. Comparing to a magnet recessed as indicated by magnets 408 and 416 that has sufficient magnetization to create a field of 10 Gauss at 4 mm from the outside of the plastic, the latter magnet would be weaker and its field strength at more than 4 mm from the outside of the plastic will be less than the field strength of the stronger magnet placed inside of the plastic.

Using a weaker magnet minimizes the risk of false triggers for medical devices that contain embedded magnetic detectors. Placing magnets 408 and 416 on the outside of their respective plastic housings places magnet 408 closer to magnetic detector 414 than would be the case if magnet 408 were located inside of plastic housing 402 and places magnet 416 closer to magnetic detector 406 than would be the case if magnet 416 were located inside of plastic housing 410. Typically, the spacing gap between magnets 416 and magnetic detector 406 and between magnet 408 and magnetic detector 414 is reduced by 2 millimeters by placing magnets 408 and 416 on the outside of their respective plastic housings.

Physical detents may be included in the plastic housing to help the user properly locate the sensor 110 relative to patient monitor 208 to trigger the proximity detection. Labels may be used over the magnets 408 and 416 and over the magnetic detectors 406 and 408 to help guide the user to place the physiological sensor 110 in proper alignment with the magnetic detector in monitor 208.

Figure 5:
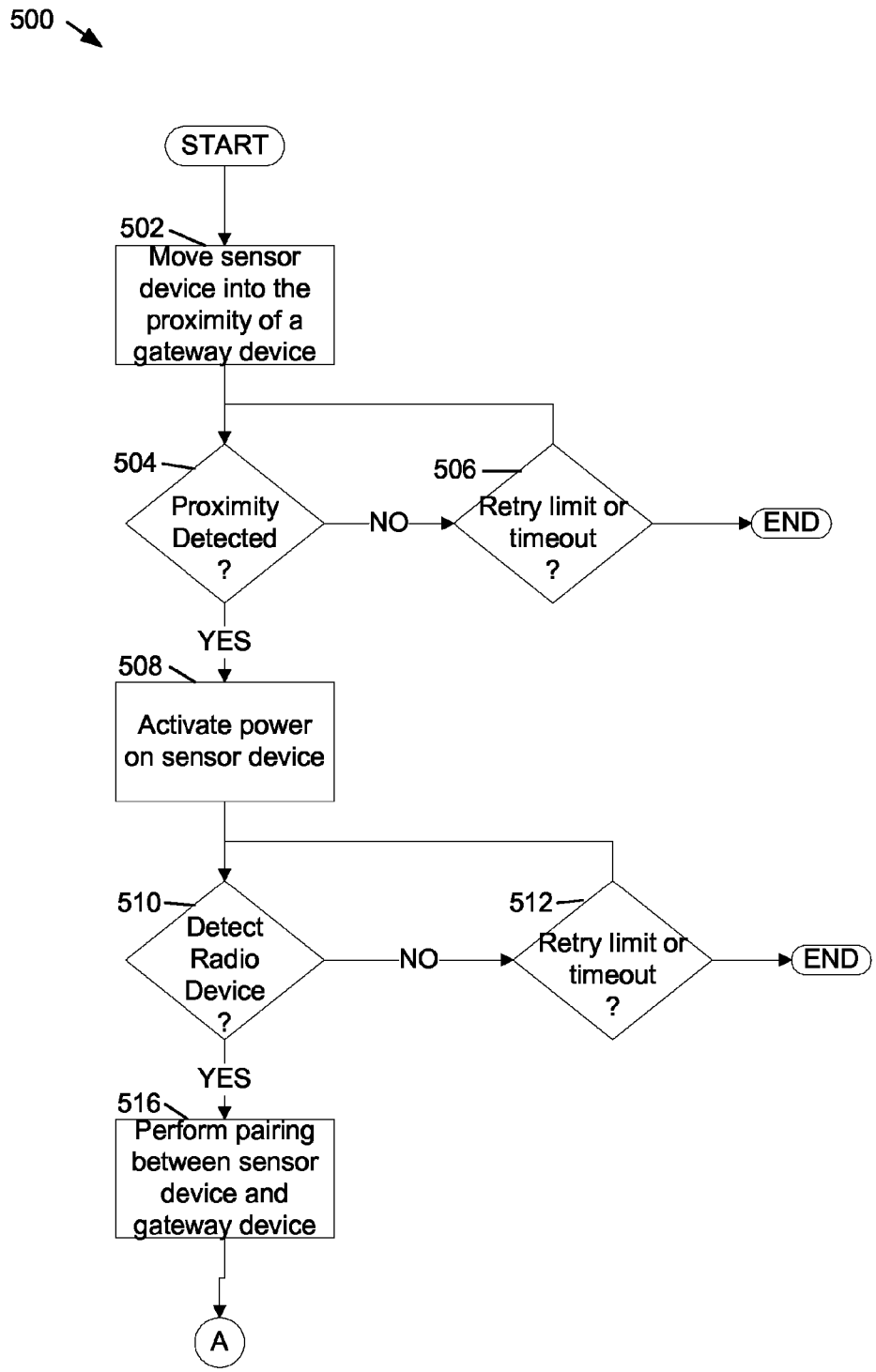
FIGS. 5 and 6 show a flowchart for a method of establishing a connection between a sensor device and a gateway device in the personal area network of FIG. 2.
Figure 6:
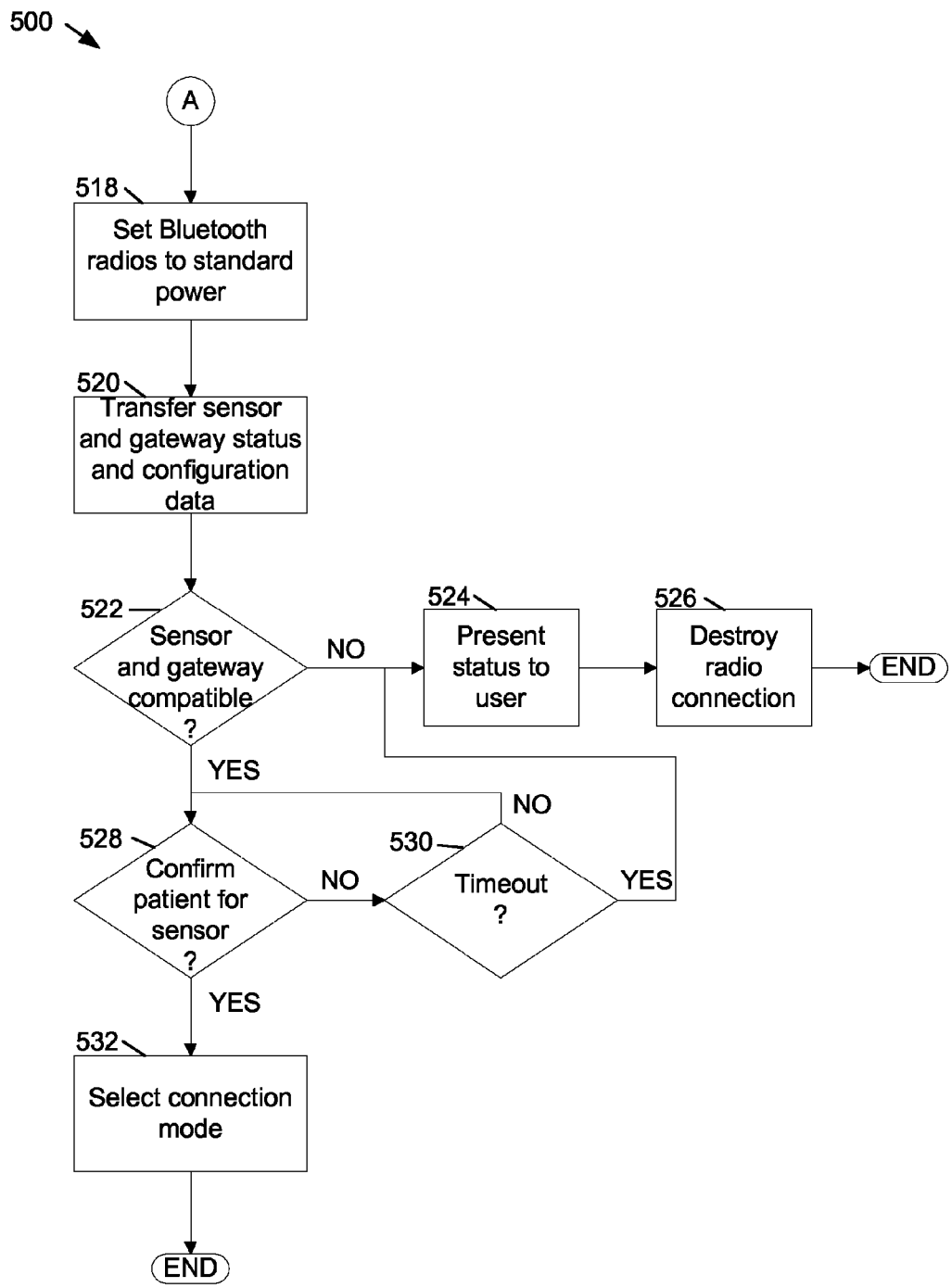

FIGS. 5 and 6 show a flowchart 500 for a method for using proximity detection to establish a connection between a sensor device, for example physiological sensor 110 and a gateway device, for example patient monitor 208. At operation 502, a radio on the sensor device is in a non-connectable state. Typically, both the radio and the sensor device are powered off. An internal retry count is set to zero.

At operation 504, a determination is made whether a proximity detector on the sensor device is activated. The proximity detector on the sensor device is typically not activated until the sensor device is proximal to the gateway device. The determination of whether the proximity detector is activated comprises whether a magnet, for example magnet 416 on the gateway device activates a magnetic detector, for example magnetic detector 406 on the sensor device. Depending on the strength of the magnet on the gateway device, the sensor device may need to be moved within centimeters of the gateway device or in some examples the sensor device may need to physically touch the gateway device in order for the magnetic detector to be activated.

When a determination is made at operation 504 that the proximity detector is not activated, control loops back to operation 502. Control loops between operation 502 and operation 504 until the proximity detector is activated.

When a determination is made at operation 504 that the proximity detector is activated, at operation 508, the Bluetooth radio on the sensor device is set to a connectable state, in low-power. This includes powering on the radio if it was not powered. The use of low-power radio transmission during connection improves security during the connection process, but is not required.

At operation 510, a determination is made as to whether the sensor device detects a second radio device, for example a Bluetooth radio, on the gateway device and whether the gateway device detects a radio device on the sensor device. Typically, proximity detection occurs near simultaneously at sensor device and the gateway device and each places its respective radio in a connectable state. This connectable state may include also being discoverable. However, the Bluetooth radio on the gateway device may turn on at a slightly different time than the Bluetooth radio on the sensor device. It is also possible that one magnetic detector was triggered and the other was not. If the out-of-band proximity detection transmits the MAC address, discovery times may be significantly decreased compared to methods such as paging.

If a determination is made at operation 510 that a second Bluetooth radio is not detected, typically because there is a slight delay in turning on power for the second Bluetooth radio, at operation 510 a retry count is incremented. At operation 512, a determination is made as to whether a retry limit has been reached. When it is determined at operation 512, that a retry limit has not been reached, control returns to operation 508 and another determination is made as to whether a second Bluetooth radio has been detected. When it is determined at operation 512, that a retry limit has been reached, control returns to operation 502 and the sensor device is put back in a non-connectable state. Alternatively, instead of a fixed number of retries, a determination may be made at operation 512 as to whether a timeout limit has been reached.

When a determination is made at operation 510 that a second Bluetooth radio has been detected, at operation 516, Bluetooth pairing is performed between the sensor device and the gateway device.

At operation 518, the radio devices are set to a standard power level and the sensor device is paired to the gateway device. For example, standard power is 4 dBm for a Class II Bluetooth radio and 20 dBm for a Class I Bluetooth radio.

At operation 520, status and configuration information are transferred between the sensor device and the gateway device. The status and configuration includes such items as the strength of a battery on the sensor device and the model and version numbers of the sensor device and the gateway device. The status and configuration information are transferred in an attempt to determine whether the sensor device is operationally compatible with the gateway device.

At operation 522, a determination is made as to whether the sensor device and the gateway device are compatible. The determination is made by comparing the model number and version of the sensor device with the model number and version number of the gateway device to a file or database indicating the set of compatible versions and models.

When it is determined at operation 522 that the sensor device and the gateway device are not compatible, at operation 524, a status message that the sensor device and gateway device are not compatible is displayed to the user. This status message might be displayed on the gateway device, the sensor device, a syslog server, through e-mail or other electronic communication. At operation 526, the logical connection between the sensor device and the gateway device is broken and the connection sequence ends. Breaking the logical connection might be at the application layer or at the RF layer and might include removing stored pairing information. The incompatibility message may be sent to a server. Alternately, the user may be prompted to confirm download of new software that corrects an incompatibility option before destroying the radio connection.

When it is determined at operation 522 that the sensor device and the gateway device are compatible, at operation 528, a message that the sensor device and the gateway device are compatible is displayed on the user interface of the gateway device and the clinician is prompted to confirm the patient for the sensor device. The confirmation of the patient to the sensor device provides an additional level of security to ensure that the sensor device is being assigned to the correct patient.

If there is no confirmation determined at operation 528, at operation 530, a determination is made as to whether the allotted wait time for the clinician has expired. If a timeout occurs, meaning that the clinician has not confirmed the patient for the sensor device within a reasonable period of time, at operation 524, a message is displayed on the user interface of the gateway device that the patient has not been confirmed for the sensor and at operation 526, the logical connection between the sensor device and the gateway device is broken. At operation 530, if the timeout limit has not been reached, then control is returned to operation 528.

When the patient has been confirmed for the sensor device, at operation 532, the connection mode is selected. As discussed, the connection mode can be one of loose pairing, tight pairing or locked. Additional connection modes may be created to support additional clinical work flows.

Figure 7:
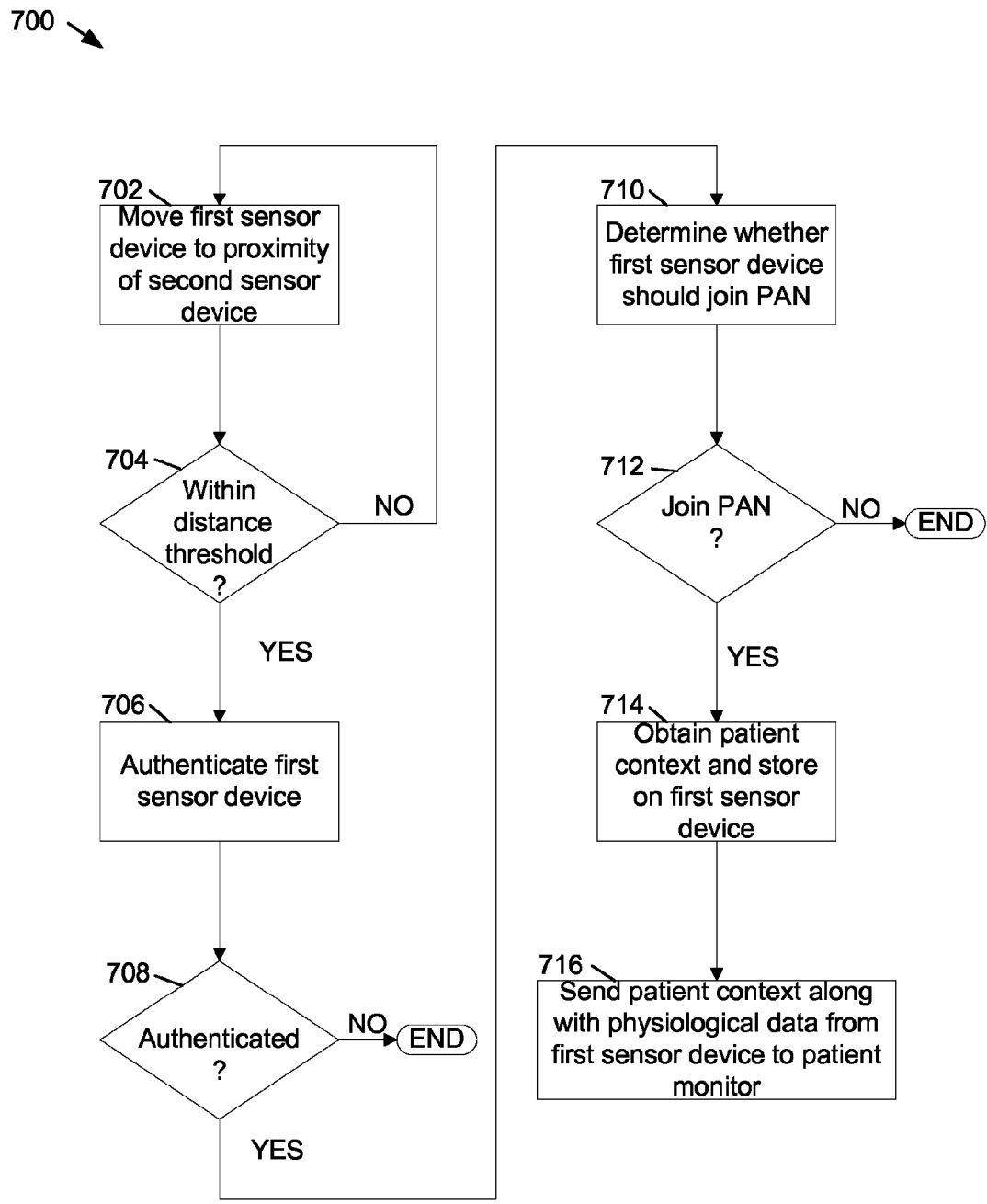
FIG. 7 shows a flowchart for a method of transferring patient context to a sensor device in the personal area network of FIG. 2.

FIG. 7 shows a flowchart for a method of transferring patient context to a first sensor device, for example to SPO2 sensor device 110. At operation 702, sensor device 110 is moved within range of a second sensor device, for example sensor device 108. As sensor device 110 is moved within range with sensor device 108, sensor device 110 sends out ranging signals to sensor device 108. The ranging signals are generated from UWB circuitry in a proximity detector on sensor device 108. It should be noted that the second sensor device may be a patient monitor.

At operation 704, a determination is made as to whether the distance between sensor device 110 and sensor device 108 is within a predetermined distance threshold. The distance threshold is a small distance, typically less than 25 cm, which provides an indication that sensor device 110 is in close proximity with sensor device 108. When the distance between sensor device 110 and sensor device 108 is less than the predetermined threshold, at operation 706 sensor device 110 is authenticated on a personal area network that includes sensor device 108. The authentication comprises sensor device 110 sending an identifier to sensor device 108. The identifier, typically a MAC address of sensor 110, is received by sensor device 108 and sent from sensor device 108 to a patient monitoring device, for example patient monitor 108. Patient monitor 108 sends the MAC address via a gateway, for example LAN/WAN gateway 218, to an EMR/EHR system. The EMR/EHR system authenticates the MAC address. When a sensor device does not have enough memory to store a MAC address, a serial number for the sensor device may be used as an identifier instead of the MAC address.

At operation 708, when sensor device 110 is authenticated, at operation 710 a determination is made as to whether the sensor device 110 should join the PAN. The determination as to whether sensor device 110 should join the PAN is typically based on multiple factors. One factor may be the distance between sensor device 110 and sensor device 108. A second factor may be the time interval that the distance between sensor device 110 and sensor device 108 is within the predetermined threshold. A third factor may be whether a physiological measurement has been made from sensor device 110. Other factors may be considered.

At operation 712, when a determination is made that sensor device 110 should join the PAN, at operation 714, patient context is obtained and stored on sensor device 110. The patient context, typically an identifier for the patient, is obtained from patient monitor 208 or from the EMR/EHR system via gateway 218. At operation 716, when physiological data is sent from sensor device 110 to patient monitor 208, the patient context is sent along with the physiological data. Sending patient context along with the physiological data helps ensure that the physiological data is identified as being associated with the correct patient and allows the sensor to upload data to any gateway, as would be useful for ambulatory patients.

Figure 8:
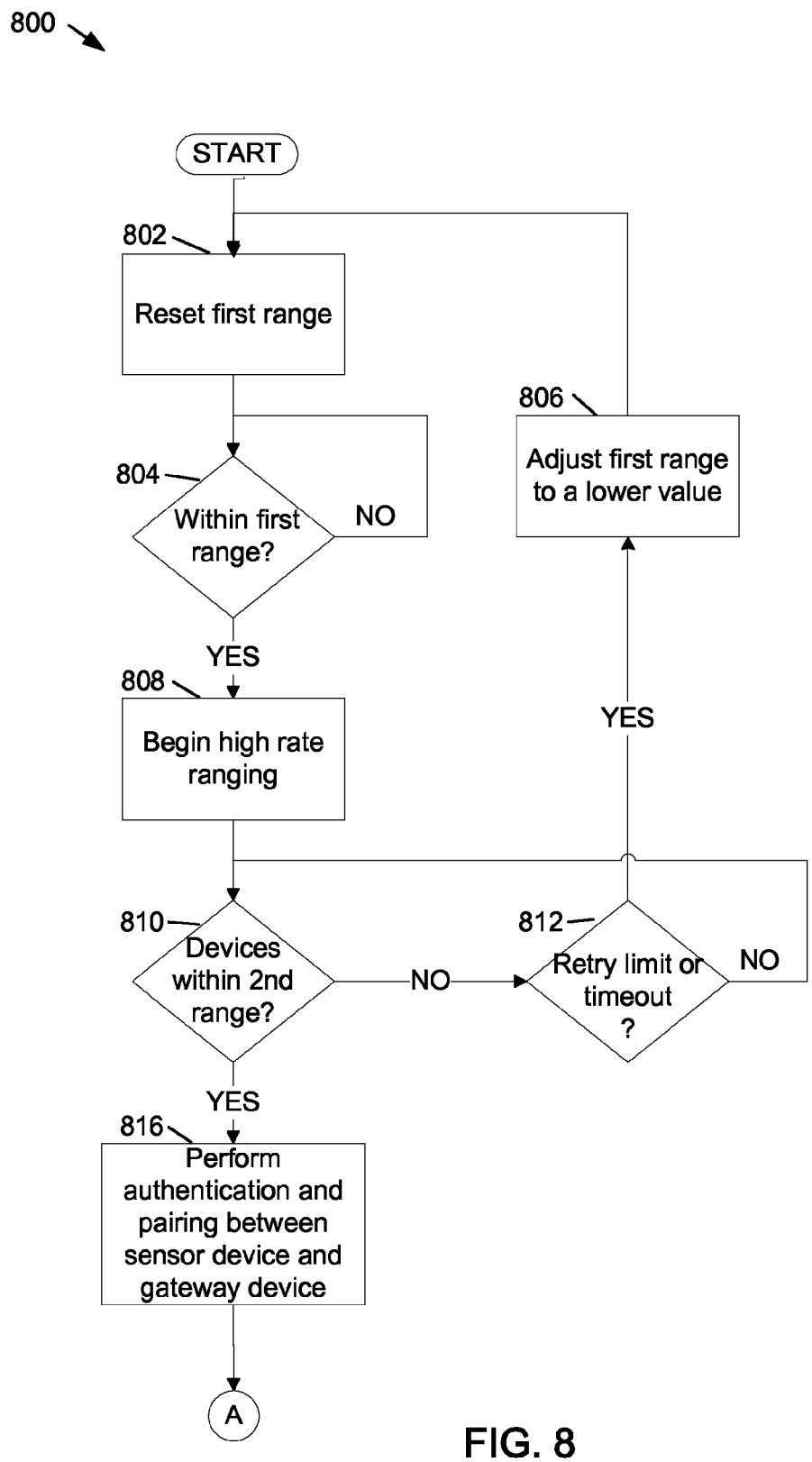
FIGS. 8 and 9 show a flowchart for a method of using ultra-wideband ranging to establish a connection between a sensor device and a gateway device in the personal area network of FIG. 2.
Figure 9:
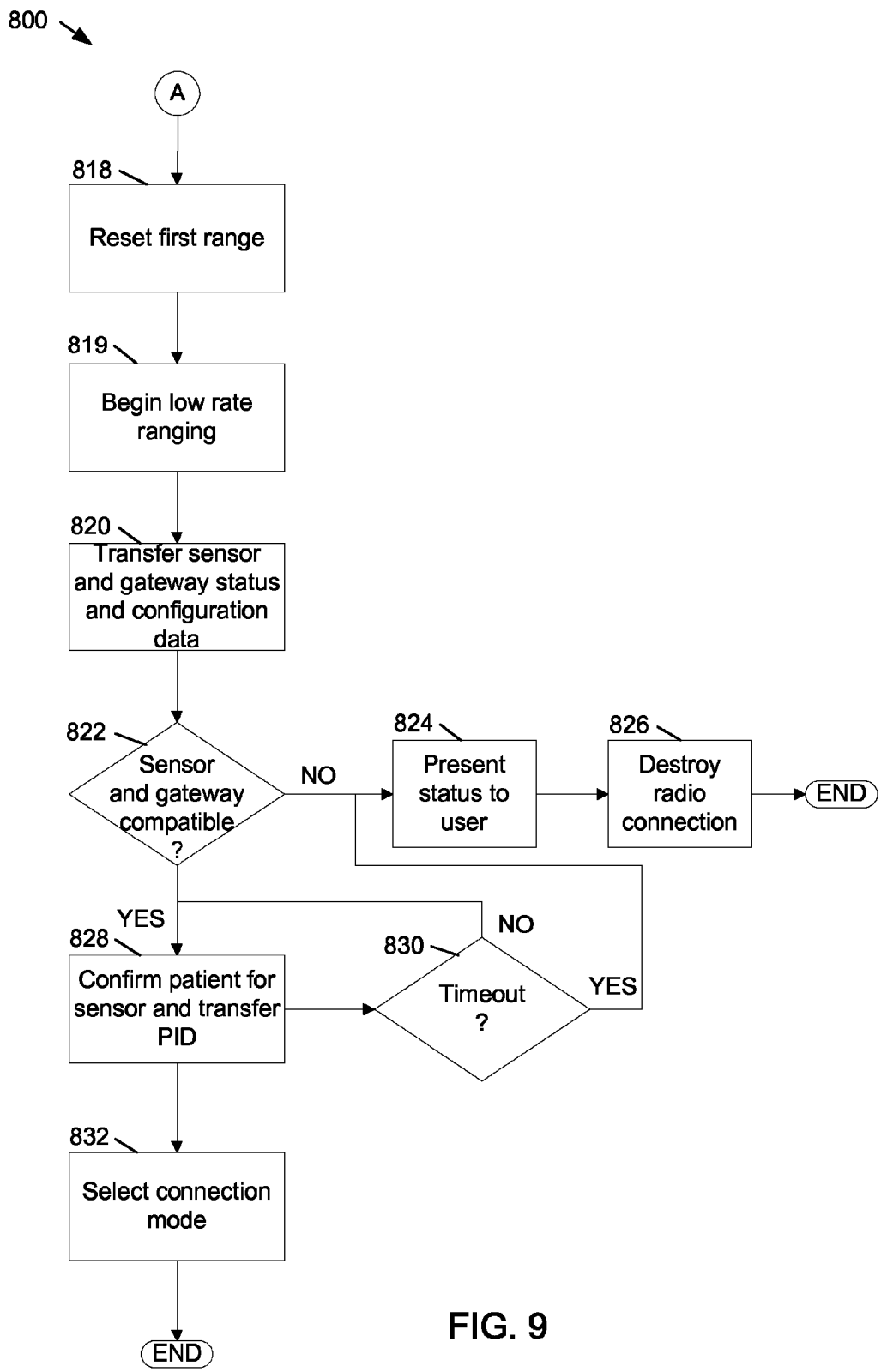

FIGS. 8 and 9 show a flowchart 800 for a method for using UWB ranging to establish a connection between a sensor device, for example physiological sensor 110 and a gateway device, for example patient monitor 208. At operation 802, a radio on the sensor device begins low rate ranging. In examples, for low rate ranging, the radio on the sensor device may send out ranging signals at a rate between one ranging signal every second to one ranging signal every 30 seconds. In other examples, different rates may be used for low rate ranging. In examples, the ranging signal may comprise more than one signal. Low rate ranging is typically used when it is unknown how far the sensor is from the gateway device. In this situation, low rate ranging may be used to conserve battery power.

At operation 804, a determination is made as to whether the gateway device is within a first range of the sensor device. In examples, the first range of the sensor device may be a distance of 5 meters. Other values for the first range may be used.

When it is determined at operation 804 that the first sensor device is not within the first range, control returns to operation 804 and another check on the first range is made. When it is determined at operation 804 that the first sensor device is within the first range, at operation 808, the radio on the sensor device begins high rate ranging. High rate ranging comprises sending out ranging signals at a higher frequency than for low rate ranging. In examples, high rate ranging may comprise sending out one or more ranging signals every 0.05 to 0.5 seconds. Other frequencies of high rate ranging may be used.

At operation 810 a determination is made as to whether the gateway device is within a second range of the sensor device. The second range is a smaller value than the first range, corresponding to a predetermined distance threshold, as discussed earlier herein. In examples, the second range may be a distance of 50 cm. Other values for the second range may be used.

When a determination is made at operation 810 that the gateway device is not within the second range of the sensor device, at operation 812 a determination is made as to whether a retry limit or timeout has been reached. When a determination is made at operation 812 that a retry limit or timeout has been reached, at operation 806, the first range is adjusted to a lower value. In examples, the first range may be reduced by 50 percent. In other examples, the first range may be reduced by a different amount. One reason for reducing the first range at operation 806 is to reduce the amount of time that the sensor may be in a high range mode, thereby conserving battery power on the sensor. Control then returns to operation 802, returning the sensor to low rate ranging. If a determination is made at operation 812 that neither a retry limit nor timeout has been reached, control is returned to operation 810.

When a determination is made at operation 810 that the sensor device is within the second range, at operation 816, range-based authentication and pairing is performed between the sensor device and the gateway device.

At operation 818, the first range is reset, typically to a default value. The first range is reset because the first range may have been changed at operation 806. At operation 819, the sensor device begins low rate ranging.

At operation 820, status and configuration information are transferred between the sensor device and the gateway device. The status and configuration includes such items as the strength of a battery on the sensor device and the model and version numbers of the sensor device and the gateway device. The status and configuration information are transferred in an attempt to determine whether the sensor device is operationally compatible with the gateway device.

At operation 822, a determination is made as to whether the sensor device and the gateway device are compatible. The determination is made by comparing the model number and version of the sensor device with the model number and version number of the gateway device to a file or database indicating the set of compatible versions and models.

When it is determined at operation 822 that the sensor device and the gateway device are not compatible, at operation 824, a status message that the sensor device and gateway device are not compatible is displayed to the user. This status message might be displayed on the gateway device, the sensor device, a syslog server, through e-mail or other electronic communication. At operation 826, the logical connection between the sensor device and the gateway device is broken and the connection sequence ends. Breaking the logical connection might be at the application layer or at the RF layer and might include removing stored pairing information. The incompatibility message may be sent to a server. Alternately, the user may be prompted to confirm download of new software that corrects an incompatibility option before destroying the radio connection.

When it is determined at operation 822 that the sensor device and the gateway device are compatible, at operation 828, a message that the sensor device and the gateway device are compatible is displayed on the user interface of the gateway device and the clinician is prompted to confirm the patient for the sensor device. In addition, the gateway device transfers patient context to the sensor device. The confirmation of the patient to the sensor device provides an additional level of security to ensure that the sensor device is being assigned to the correct patient. In some conditions when it is there is no ambiguity as to whether the patient should be confirmed for the sensor, the system may automatically confirm the patient for the sensor and transfer the PID.

If there is no confirmation determined at operation 828, at operation 830, a determination is made as to whether the allotted wait time for the clinician has expired. If a timeout occurs, meaning that the clinician has not confirmed the patient for the sensor device within a reasonable period of time, at operation 824, a message is displayed on the user interface of the gateway device that the patient has not been confirmed for the sensor and at operation 826, the logical connection between the sensor device and the gateway device is broken. At operation 830, if the timeout limit has not been reached, then control is returned to operation 828.

When the patient has been confirmed for the sensor device, at operation 832, the connection mode is selected. As discussed, the connection mode can be one of loose pairing, tight pairing or locked. Additional connection modes may be created to support additional clinical work flows.

A physiological sensor and monitor that incorporate Bluetooth technology are computing devices and typically include at least one processing unit, system memory and a power source. Depending on the exact configuration and type of computing device, the system memory may be physical memory, such as volatile memory (such as RAM), non-volatile memory (such as ROM, flash memory, etc.) or some combination of the two. System memory typically includes an embedded operating system suitable for controlling the operation of the sensor device. The system memory may also include one or more software applications, for example Bluetooth, and may include program data.

The various embodiments described above are provided by way of illustration only and should not be construed to limiting. Various modifications and changes that may be made to the embodiments described above without departing from the true spirit and scope of the disclosure.

What is claimed is:

1. A wireless medical device, the wireless medical device comprising:
    a processor;
    a memory that stores a patient context, the patient context providing an identifier for the patient;
    a radio comprising an ultra-wideband (UWB) transceiver that determines a distance between the wireless medical device and a second wireless medical device, the radio using the distance as part of an authentication process;
    wherein the wireless medical device is configured to join a personal area network with the second wireless medical device when the distance between the wireless medical device and the second wireless medical device is within a predetermined threshold, the distance being greater than zero, wherein the wireless medical device is configured to obtain the patient context from the second wireless medical device, the patient context being obtained from the second wireless medical device when the distance between the wireless medical device and the second wireless medical device is within the predetermined threshold for at least a predetermined interval of time, wherein the wireless medical device is configured to transfer physiological data to the second wireless medical device, the physiological data being transferred along with the patient context, and
    wherein the wireless medical device is configured to support a spot check mode and a continuous workflow mode, wherein when a second distance determined by the radio between the wireless medical device and the second wireless monitor device is greater than a second predetermined threshold for at least a second predetermined interval of time, the patient context data is removed from the wireless medical device if the wireless medical device is operating in a spot check mode and the patient context data remains stored on the wireless medical device if the wireless medical device is operating in a continuous workflow mode.

2. The wireless medical device of claim 1, wherein the patient context is obtained from the second wireless medical device upon the detection of physiological signals by the wireless medical device while within the first predetermined threshold.

3. The wireless medical device of claim 1, wherein the second wireless medical device is a patient monitor device.

4. The wireless medical device of claim 1, wherein the patient context is removed from the wireless medical device based on conditions determined by a clinical workflow definition for the wireless medical device.

5. The wireless medical device of claim 1, wherein the patient context is further removed from the wireless medical device when a time since a physiological measurement has been made at the wireless medical device is greater than another predetermined time interval.

6. The wireless medical device of claim 1, wherein the patient context is a medical device identifier.

7. The wireless medical device of claim 1, wherein the wireless medical device is powered on when the distance between the wireless medical device and the second wireless medical device is within a pre-determined threshold.

8. The wireless medical device of claim 1, wherein the wireless medical device creates or breaks a connection based on conditions determined by a clinical workflow definition for the wireless medical device.

9. The wireless medical device of claim 1, wherein a ranging functionality is used to respond to queries.

10. The wireless medical device of claim 1, wherein the wireless medical device changes state based upon a detection of motion of the wireless medical device.

11. A method for authenticating a connection between two wireless medical devices, the method comprising:
    moving a first wireless medical device to a proximity of a second wireless medical device;
    using a first proximity detector on the first wireless medical device to determine a first distance between the first wireless medical device and the second wireless medical device;
    joining the first and second wireless medical devices to a personal area network when the first distance between the first wireless medical device and the second wireless medical device is within a first predetermined threshold, the first distance being greater than zero;
    obtaining a patient context at the first wireless medical device from the second wireless medical device when the first distance between the first wireless medical device and the second wireless medical device is within the first predetermined threshold for at least a first predetermined interval of time;
    transferring physiological data to the second wireless medical device along with the patient context;
    using the first proximity detector to determine a second distance;
    determining that the second distance is greater than a second predetermined threshold for at least a second predetermined period of time;
    removing the patient context data from the first wireless medical device if the first wireless medical device is operating in a spot check mode; and maintaining the patient context data stored in the first wireless medical device if the first wireless medical device is operating in a continuous workflow mode.

12. The method of claim 11, wherein the first distance between the first wireless medical device and the second wireless medical device is obtained using an ultra-wideband ranging capability of the first wireless medical device and the second wireless medical device.

13. A system for transmitting physiological data from a first wireless medical device, the system comprising the first wireless medical device and a patient monitor device, the first wireless medical device comprising:
- a first processor;
- a first memory that stores a patient context, the patient context providing an identifier for the patient; and
- a first radio, the first radio comprising a first ultra-wideband (UWB) transceiver that determines a first distance between the first wireless medical device and the patient monitor device, the first radio using the first distance as part of an authentication process, the patient monitor device comprising:
- a second processor;
- a second memory that stores the patient context; and
- a second radio, the second radio comprising a second UWB transceiver, wherein the first wireless medical device joins a personal area network with the patient monitor device when the first distance between the first wireless medical device and the patient monitor device is within a first predetermined threshold, the first distance being greater than zero, wherein the first wireless medical device obtains the patient context from the patient monitor device, the patient context being obtained from the patient monitor device when the first distance between the first wireless medical device and the patient monitor device is within the first predetermined threshold for at least a first predetermined interval of time, wherein the first wireless medical device transfers physiological data to the patient monitor device, the physiological data being transferred along with the patient context, and wherein the first wireless medical device supports a spot check mode and a continuous workflow mode, wherein when a second distance determined by the first radio between the first wireless medical device and the patient monitor device is greater than a second predetermined threshold for at least a second predetermined interval of time, the patient context data is removed from the first wireless medical device if the first wireless medical device is operating in a spot check mode and the patient context data remains stored on the first wireless medical device if the first wireless medical device is operating in a continuous workflow mode.

14. The system of claim 13, wherein the patient monitor device presents a confirmation request prior to storing the patient context when the range to multiple patient monitor devices is within a pre-determined threshold.

* * * * *